(12) United States Patent
Lee

(10) Patent No.: US 7,071,215 B2
(45) Date of Patent: Jul. 4, 2006

(54) ANTHELMINTIC AND INSECTICIDAL COMPOSITIONS

(75) Inventor: Byung Hyun Lee, Kalamazoo, MI (US)

(73) Assignee: Pharmacia & Upjohn Company LLC, Kalamazoo, MI (US)

( * ) Notice: Subject to any disclaimer, the term of this patent is extended or adjusted under 35 U.S.C. 154(b) by 422 days.

(21) Appl. No.: 10/687,496

(22) Filed: Oct. 16, 2003

(65) Prior Publication Data

US 2004/0127548 A1 Jul. 1, 2004

Related U.S. Application Data

(60) Provisional application No. 60/419,133, filed on Oct. 17, 2002.

(51) Int. Cl.
*A61K 31/445* (2006.01)
*A61K 31/38* (2006.01)
*C07D 401/00* (2006.01)
*C07D 333/36* (2006.01)

(52) U.S. Cl. ............... 514/326; 514/445; 546/209; 549/63

(58) Field of Classification Search ........... 514/326, 514/445; 546/209; 549/63
See application file for complete search history.

(56) References Cited

U.S. PATENT DOCUMENTS

| | | | |
|---|---|---|---|
| 5,095,032 A | 3/1992 | Bertram et al. ............. 514/443 |
| 5,773,442 A | 6/1998 | Akamatsu et al. .......... 514/255 |
| 5,859,188 A | 1/1999 | Geary et al. ................ 530/329 |
| 6,414,013 B1 * | 7/2002 | Fancelli et al. ............. 514/438 |
| 6,762,183 B1 * | 7/2004 | Fischer et al. ............. 514/242 |
| 6,881,741 B1 * | 4/2005 | Chan Chun Kong et al. .... 514/326 |

FOREIGN PATENT DOCUMENTS

EP   0 495 473   1/1992

OTHER PUBLICATIONS

Berge et al., J. *Miami. Sci.*, 66:1-19 (1977).
Perrissin, M., et. al., *Eur. J. Med. Chem.—Chim. Ther.*, 15(5), 413-18, (1980).

* cited by examiner

*Primary Examiner*—Deborah C. Lambkin
(74) *Attorney, Agent, or Firm*—Timothy J. Gumbleton

(57) ABSTRACT

Novel anthelmintic compositions containing thiophene derivatives as active ingredients are disclosed.

14 Claims, No Drawings

ANTHELMINTIC AND INSECTICIDAL COMPOSITIONS

CROSS REFERENCE

This application claims the benefit of the following provisional application: U.S. Ser. No. 60/419,133, filed Oct. 17, 2002 under 35 USC 119(e)(i), which is incorporated herein by reference in its entirety.

BACKGROUND OF THE INVENTION

1. Field of the Invention

The present invention relates to novel anthelmintic and insecticidal compositions in general, and, more specifically, compositions containing thiophene derivatives as active ingredients.

2. Technology Description

Control of parasitic infections in human and animal populations remains an important global endeavor. The causative organisms may be categorized as endoparasitic members of the classes Nematoda, Cestoidea and Trematoda or phylum Protozoa, or as ectoparasitic members of the phylum Arthropoda. The former comprises infections of the stomach, intestinal tracts, lymphatic system, tissues, liver, lungs, heart and brain. Examples include trichinosis, lymphatic filariasis, onchocerciasis, schistosomiasis, leishmaniasis, trypanosomiasis, giardiasis, coccidiosis and malaria. The latter ectoparasites include lice, ticks, mites, biting flies, fleas and mosquitoes. These often serve as vectors and intermediate hosts to endoparasites for transmission to human or animal hosts. While certain helminthiases can be treated with known drugs, evolutionary development of resistance necessitates a further search for improved efficacy in next generation anthelmintic agents.

The control of ectoparasites, such as fleas, ticks, biting flies and the like, has long been recognized as an important aspect of human and animal health regimens. Traditional treatments were topically applied, such as the famous dips for cattle, and indeed such treatments are still in wide use. The more modern thrust of research, however, has been towards compounds, which can be administered orally, or parenterally to the animals and which will control ectoparasitic populations by poisoning individual parasites when they ingest the blood of a treated animal.

The control of endoparasites, especially intestinal parasites, has also been an important aspect of human and animal health regimens. Although a number of ectoparasiticides and endoparasiticides are in use, these suffer from a variety of problems, including a limited spectrum of activity, the need for repeated treatment and, in many instances, resistance by parasites. The development of novel endo- and ectoparasiticides is therefore essential to ensure safe and effective treatment of a wide range of parasites over a long period of time.

Despite the above teachings, there still exists a need in the art for treatment of pests.

BRIEF SUMMARY OF THE INVENTION

In accordance with the present invention, a novel composition of matter that is capable of treatment of pests is provided. The composition contains thiophene derivatives of Formula I as active ingredients:

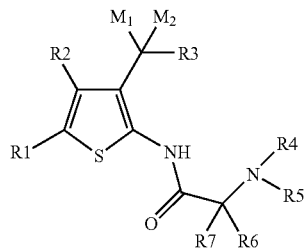

Formula I wherein:

$R_1$ and $R_2$ are selected from the group consisting of H, alkyl, phenyl, substituted phenyl, benzyl, substituted benzyl, heteroaryl, substituted heteroaryl, hetroarylmethylene, and substituted hetroaryhmethylene; or $R_1$ and $R_2$, along with the carbons to which they are attached, may form a 5- to 10-membered substituted or unsubstituted carbocyclic or heterocycloalkyl ring;

$R_3$ is alkyl, heteroalkyl, cycloalkyl, substituted or unsubstituted aryl, or substituted or unsubstituted heteroaryl;

$R_4$ and $R_5$ are independently H, alkyl, heteroalkyl, cycloalkyl, aryl, aralkyl, heteroaryl or heteroaralkyl;

$R_4$ and $R_5$ taken together with the nitrogen to which they are attached, may form a 3- to 8-membered substituted or unsubstituted nitrogen containing ring;

$R_6$ and $R_7$ are independently alkyl, heteroalkyl, aryl, aralkyl, heteroaryl or heteroaralkyl;

$M_1$ is hydrogen and $M_2$ is —OH; or $M_1$ and $M_2$ taken together may form a carbonyl (C=O).

DETAILED DESCRIPTION OF THE EMBODIMENTS

Definitions

In describing the embodiments, certain terminology will be utilized for the sake of clarity. Such terminology is intended to encompass the recited embodiments, as well as all technical equivalents that operate in a similar manner for a similar purpose to achieve a similar result.

The term "alkyl" by itself or as part of another substituent means, unless otherwise stated, a straight or branched chain, or cyclic hydrocarbon radical, or combination thereof, which may be fully saturated, mono- or polyunsaturated and can include di- and multivalent radicals, having 1 to 8 carbon atoms. Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 2-propynyl, 3-butynyl, and the higher homologs and isomers.

The term "alkylene" by itself or as part of another substituent means a divalent radical derived from an alkane, as exemplified by —CH$_2$CH$_2$CH$_2$CH$_2$—. A "lower alkyl" or "lower alkylene" is a shorter chain alkyl or alkylene group, having 8 or fewer carbon atoms.

The terms "alkoxy", "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NRR' wherein the R groups can be the same or different alkyl groups.

The term "heteroalkyl" by itself or in combination with another term means, unless otherwise stated, a stable straight or branched chain, or cyclic hydrocarbon radical, or combinations thereof, fully saturated or containing from 1 to 3 degrees of unsaturation, consisting of the stated number of carbon atoms and from 1 to 3 heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Also included in the term "heteroalkyl" are those radicals described in more detail below as "heterocycloalkyl."

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl" by themselves or in combination with other terms represent, unless otherwise stated, cyclic versions of "alkyl" and "heteroalkyl" respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-piperidinyl, 2-piperidinyl, 3-piperidinyl, 4-morpholinyl, 3morpholinyl, tetraliydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen" by themselves or as part of another substituent mean, unless otherwise stated, a fluorine, chlorine, bromine, or iodine atom Additionally, terms such as "fluoroalkyl" are meant to include monofluoroalkyl and polyfluoroalkyl.

The term "aryl" employed alone or in combination with other terms (e.g., aryloxy, arylthioxy, aralkyl) means, unless otherwise stated, an aromatic substituent that can be a single ring or multiple rings (up to three rings) that are fused together or linked covalently.

The term "heteroaryl" is meant to include those aryl rings which contain from 0 to 4 heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom Non-limiting examples of aryl and heteroaryl groups include phenyl, 1-naphthyl, 2-naplithyl, 4-biphenyl, 1-pyrrolyl, 2-pyrrolyl, 3-pyrrolyl, 3-pyrazolyl, 4-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5thiazolyl, 2-furyl, 3-furyl, 2-thienyl, 3-thienyl, 2.7pyridyl, 3-pyridyl, 4-pyridyl, 2-pyrimidyl, 4-pyrimidyl, 5-benzothiazolyl, purinyl, 2-benzimidazolyl, 5-indolyl, lisoquinolyl, 5-isoquinolyl, 2-quinoxalinyl, 5-quinoxalinyl, 3-quinolyl, and 6-quinolyl.

Substituents for each of the above noted aryl ring systems are selected from the group of acceptable substituents described below.

The term "aralkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R"—SR', -halogen, —SiR'R"R, —OC(O)R', —C(O)R', —$CO_2$R', CONR'R", —OC(O)NR'R"—NR'C(O)R', —NR'—C(O)NR"R'", —NR'COOR', —NH—C($NH_2$)=NH, —NR'C($NH_2$)=N—H, —NH—C($NH_2$)=NR', —S(O)R', S(O)$_2$R', —S(O)$_2$NR'R", —CN and —$NO_2$ in a number ranging from zero to (2N+1), where N is the total number of carbon atoms in such radical. R', R" and X" each independently refer to hydrogen, unsubstituted (Cl-COalkyl and heteroalkyl, unsubstituted aryl, aryl substituted with 1 to 3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl, (unsubstituted aryl)-($C_1$–$C_4$)alkyl, and (unsubstituted aryloxy-($C_1$–$C_4$)alkyl.

Two of the substituents on adjacent atoms of the aryl ring may optionally be replaced with a substituent of the formula -T-C(O)—($CH_2$)$_q$-U-, wherein T and U are independently —NH—, —O—, —$CH_2$— or a single bond, and the subscript q is an integer of from 0 to 2. Alternatively, two of the substituents on adjacent atoms of the aryl ring may optionally be replaced with a substituent of the formula -A-($CH_2$),-B-, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —($CH_2$), —X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" means oxygen (O), nitrogen (N), and sulfur (S).

Room temperature means 18–25° C.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactouronic acids and the like (see, for example, Berge et al., (1977) *J. Miami. Sci.,* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention that is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

DETAILED DESCRIPTION OF THE INVENTION

One embodiment of the present invention provides a compound of Formula I:

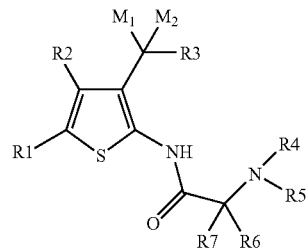

Formula I wherein:

R$_1$ and R$_2$ are selected from the group consisting of H, alkyl, phenyl, substituted phenyl, benzyl, substituted benzyl, heteroaryl, substituted heteroaryl, hetroaylmethylene, and substituted hetroarylmethylene; or R$_1$ and R$_2$, along with the carbons to which they are attached, may form a 5- to 10-membered substituted or unsubstituted carbocyclic or heterocycloalkyl ring;

R$_3$ is alkyl, heteroalkyl, cycloalkyl, substituted or unsubstituted aryl, or substituted or unsubstituted heteroaryl;

R$_4$ and R$_5$ are independently H, alkyl, heteroalkyl, cycloalkyl, aryl, aralkyl, heteroaryl or heteroaralkyl;

R$_4$ and R$_5$ taken together with the nitrogen to which they are attached, may form a 3- to 8-membered substituted or unsubstituted nitrogen containing ring;

R$_6$ and R$_7$ are independently alkyl, heteroalkyl, aryl, aralkyl, heteroaryl or heteroaralkyl;

M$_1$ is hydrogen and M$_2$ is —OH; or

M$_1$ and M$_2$ taken together may form a carbonyl (C=O).

A second embodiment of the present invention provides a composition comprising a compound of Formula I and a carrier.

Another embodiment of the present invention comprises a process for the treatment or prevention of parasitic diseases in mammals, including humans, plants or agricultural crops comprising the step of administering to the mammal, plant or crop an effective amount of the above composition.

A further embodiment of the present invention comprises the use of the above-described composition to prepare a medicament for the treatment or prevention of parasitic diseases in mammals.

Yet another embodiment of the present invention comprises the above-described composition for use as a medicament.

An object of the present invention is to provide novel compositions that can be broadly used against parasites.

Still another object of the present invention is to provide a method for preventing or treating parasitic diseases in mammals by using a novel composition.

A further object of the present invention is to provide a method for producing a medicament using a novel composition.

These, and other objects, will readily be apparent to those skilled in the art.

In practice, the amount of the compound to be administered ranges from about 0.001 to 10 mg. per kg. of animal body weight, such total dose being given at one time or in divided doses over a relatively short period of time such as 1 to 5 days. Control of such parasites is obtained in animals by administering from 0.02 to 30 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

For use as an antiparasitic agent in animals, the inventive composition may be administered internally either orally or by injection, or topically as a liquid drench or as a shampoo. These compositions may be administered orally in a unit dosage form such as a capsule, bolus or tablet. The drench is normally a solution, suspension or dispersion of the active ingredients usually in water together with a suspending agent such as bentonite and a wetting agent or like excipient. Generally, the drenches also contain an antifoaming agent. Drench formulations generally contains from about 0.01 to 10% by weight of each active compound. Preferred drench formulations may contain from 0.05 to 5.0% of each active by weight. The capsules and boluses comprise the active ingredients admixed with a carrier vehicle such as starch, talc, magnesium stearate, or di-calcium phosphate.

Where it is desired to administer the inventive composition in a dry, solid unit dosage form, capsules, boluses or tablets containing the desired amount of active compounds usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active composition is to be administered via an animal feedstuff, it is intimately dispersed in the feed or used as a top dressing or in the form of pellets which may then be added to the finished feed or optionally fed separately.

Alternatively, the antiparasitic compositions of the present invention may be administered to animals parenterally, for example, by intraruminal, intramuscular, intratracheal, or subcutaneous injection in which event the active ingredients are dissolved or dispersed in a liquid carrier vehicle. For parenteral administration, the active materials are suitably admixed with an acceptable vehicle, preferably of the vegetable oil variety such as peanut oil, cottonseed oil and the like. Other parenteral vehicles such as organic preparation using solketal, propylene glycol, glycerol formal, and aqueous parenteral formulations are also used, often in combination in various proportions. Still another carrier that can be selected is either N-methylpyrrolidone or 2-pyrrolidone and mixtures of the two. This formulation is described in greater detail in U.S. Pat. No. 5,773,442. To the extent necessary for completion, this patent is expressly incorporated by reference. The active compound or compounds are dissolved or suspended in the parenteral formulation for administration; such formulations generally contain from 0.005 to 5% by weight of each active compound.

In an example of the embodiment, the carrier contains propylene glycol (1–99 percent by weight of the carrier) and glycerol formal (99–1 percent by weight of the carrier), with the relative amounts being 60% propylene glycol and 40% glycerol formal.

The present compositions may also be useful in yet another method in which the same active agents as above defined are employed as a "feed through larvicide." In this method, the compound is administered to a vertebrate animal, especially a warm-blooded animal, in order to inhibit parasitic organisms that live in the feces of the animal. Such organisms are typically insect species in the egg or larval stage.

The inventive compositions are primarily useful as antiparasitic agents for the treatment and/or prevention of helminthiasis in all mammals, which includes, but is not limited to, humans, cattle, sheep, deer, horses, dogs, cats, goats, swine, and poultry. They are also useful in the prevention and treatment of parasitic infections of these mammals by ectoparasites such as ticks, mites, lice, fleas and the like. In treating such infections the inventive compositions may be used individually or in combination with each other or with other unrelated antiparasitic agents.

The exact dosage and frequency of administration of the inventive compositions depend on many factors, including (but not limited to) the severity of the particular condition being treated, the age, weight, and general physical condition of the particular patient (human or animal), and other medication the patient may be taking. These factors are well known to those skilled in the art, and the exact dosage and frequency of administration can be more accurately determined by measuring the concentration of the inventive composition in the patient's blood and/or the patient's response to the particular condition being treated.

The inventive compositions may also be used to combat agricultural pests that attack crops either in the field or in storage. The inventive compositions are applied for such uses as sprays, dusts, emulsions and the like either to the growing plants or the harvested crops. The techniques for applying the inventive compositions in this manner are known to those skilled in the agricultural arts.

Accordingly, it can be seen that the present methods can be utilized for protection against a wide range of parasitic organisms. Further, it should be noted that protection is achieved in animals with existing parasitic infections by eliminating the existing parasites, and/or in animals susceptible to attack by parasitic organisms by preventing parasitic attack. Thus, protection includes both treatment to eliminate existing infections and prevention against future infestations.

Representative parasitic organisms include the following:

Platyhelminthes:
Trematoda such as
  *Clonorchis*
  *Echinostoma*
  *Fasciola hepatica* (liver fluke)
  *Fasciola gigantica*
  *Fascioloides magna*
  *Fasciolopsis*
  *Metagonimus*
  *Paragonimus*
  *Schistosoma* spp.

Nemathelminthes:
  *Ancylostoma*
  *Angiostrongylus*
  *Anisakis*
  *Ascaris*
  *Brugia*
  *Bunostomum*
  *Cooperia*
  *Cyathostomum*
  *Cylicocyclus*
  *Dictyocaulus* (lungworm)
  *Dipetalonema*
  *Dirofilaria* (heartworm)
  *Dracunculus*
  *Elaeophora*
  *Gaigeria*
  *Globocephalus urosubulatus*
  *Haemonchus*
  *Metastrongylus* (lungworm)
  *Muellerius* (lungworm)
  *Necator americanus*
  *Nematodirus*
  *Oesophagostomum*
  *Onchocerca*
  *Ostertagia*
  *Parascaris*
  *Protostrongylus* (lungworm)
  *Setaria*
  *Stephanofilaria*
  *Syngamus*
  *Teladorsagia*
  *Toxascaris*
  *Toxocara*
  *Trichinella*
  *Trichostrongylus*
  *Uncinaria stenocephala*
  *Wuchereria bancrofti*

Arthropoda:
Crustacea:
  *Argulus*
  *Caligus*

Arachnida:
  *Amblyomma americanum* (Lone-star tick)
  *Amblyomma maculatum* (Gulf Coast tick)
  *Argas persicus* (fowl tick)
  *Boophilus microplus* (cattle tick)
  *Demodex bovis* (cattle follicle mite)
  *Demodex canis* (dog follicle mite)
  *Dermacentor andersoni* (Rocky Mountain spotted fever tick)
  *Dermacentor variabilis* (American dog tick)
  *Dermanyssus gallinae* (chicken mite)
  *Ixodes ricinus* (common sheep tick)
  *Knemidokoptes gallinae* (deplumming mite)
  *Knemidokoptes mutans* (scaly-leg mite)
  *Otobius megnini* (ear tick)
  *Psoroptes equi* (scab mite)
  *Psoroptes ovis* (scab mite)
  *Rhipicephalus sanguineus* (brown dog tick)
  *Sarcoptes scabiei* (mange mite)

Insecta:
  *Aedes* (mosquito)
  *Anopheles* (mosquito)
  *Culex* (mosquito)
  *Culiseta* (mosquito)
  *Bovicola bovis* (cattle biting louse)
  *Callitroga hominivorax* (blowfly)
  *Chrysops* spp. (deer fly)
  *Cimex lectularius* (bed bug)
  *Ctenocephalis canis* (dog flea)
  *Ctenocephalis fells* (cat flea)
  *Culicoides* spp. (midges, sandflies, punkies, or no-see-ums)
  *Damalinia ovis* (sheep biting louse)
  *Dermaobia* spp. (warble fly)
  *Dermatophilus* spp. (fleas)
  *Gasterophilus haemorrhoidalis* (nose bot fly)
  *Gasterophilus intestinalis* (common horse bot fly)
  *Gasterophilus nasalis* (chin fly)
  *Glossina* spp. (tsetse fly)
  *Haematobia irritans* (horn fly, buffalo fly)
  *Haematopinus asini* (horse sucking louse)
  *Haematopinus eurysternus* (short nosed cattle louse)
  *Haematopinus ovilius* (body louse)
  *Haematopinus suis* (hog louse)
  *Hydrotaea irritans* (head fly)
  *Hypoderma bovis* (bomb fly)
  *Hypoderma lineatum* (heel fly)
  *Linognathus ovillus* (body louse)
  *Linognathus pedalis* (foot louse)
  *Linognathus vituli* (long nosed cattle louse)
  *Lucilia* spp. (maggot fly)
  *Melophagus ovinus* (sheep ked)
  *Oestrus ovis* (nose bot fly)
  *Phormia regina* (blowfly)
  *Psorophora*
  *Reduviid* bugs (assassin bug)
  *Simulium* spp. (black fly)
  *Solenopotes capillatus* (little blue cattle louse)
  *Stomoxys calcitrans* (stable fly)
  *Tabanus* spp. (horse fly)

Parasitic organisms that live in feces are typically the egg and larval stages of insects such as:
  *Musca domestica* (housefly)
  *Musca auturnalis* (face fly)
  *Haematobia* spp. (horn fly, buffalo fly and others).

Non-limiting examples of the invention are given in Table 1.
TABLE 1
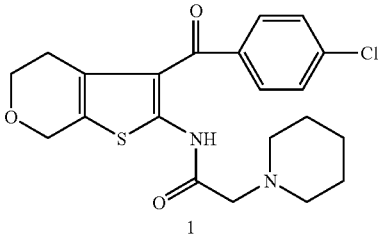
1
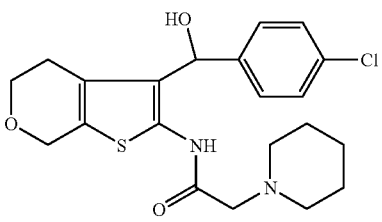
2
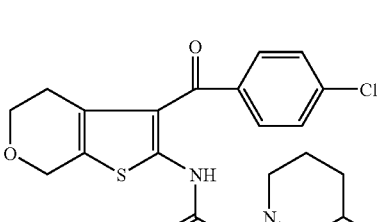
3
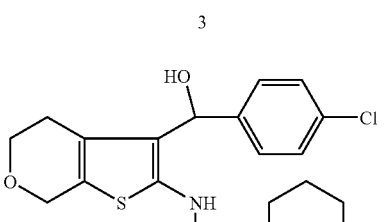
4
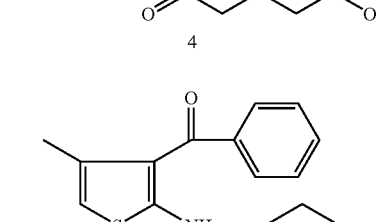
5
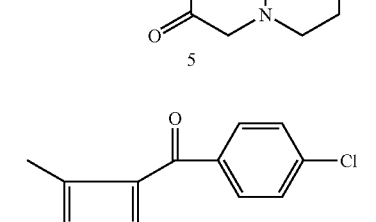
6
TABLE 1-continued
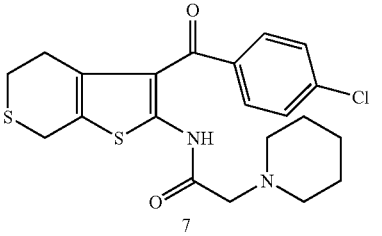
7
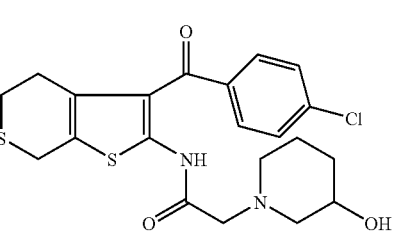
8
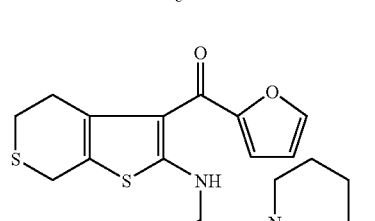
9
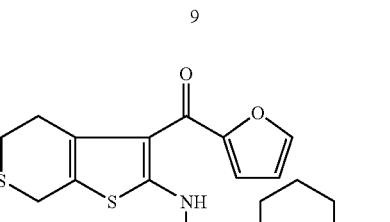
10
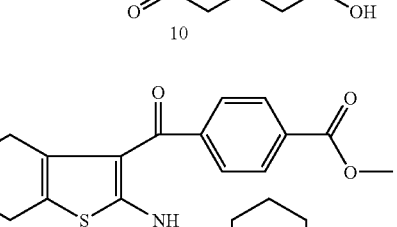
11
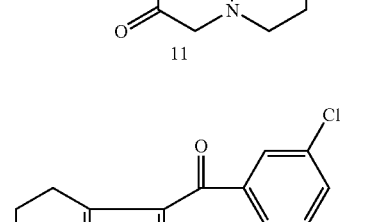
12

TABLE 1-continued
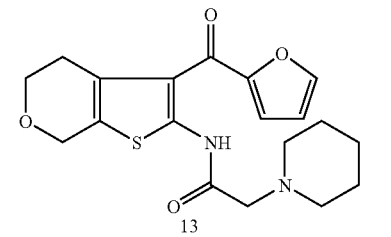
13
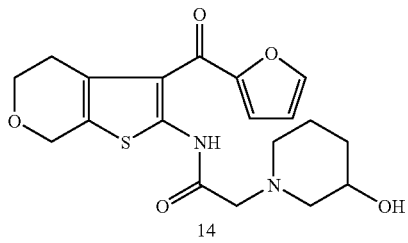
14
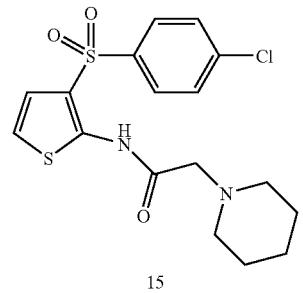
15
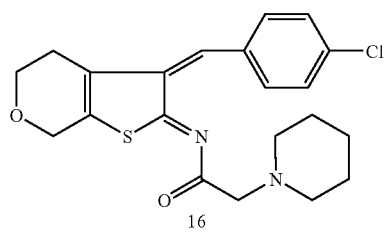
16
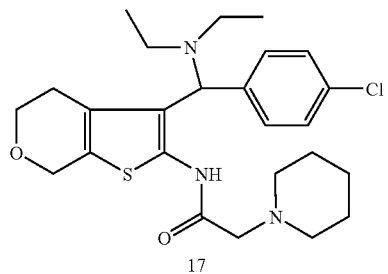
17
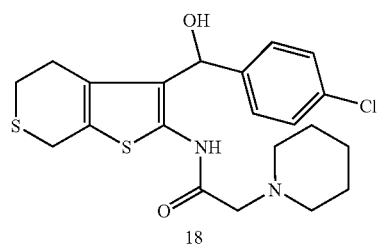
18
TABLE 1-continued
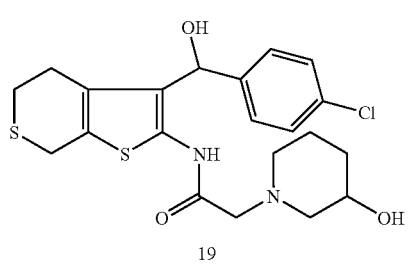
19
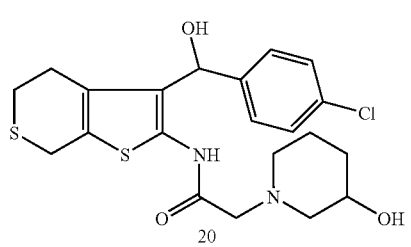
20
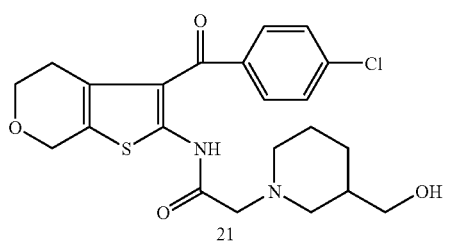
21
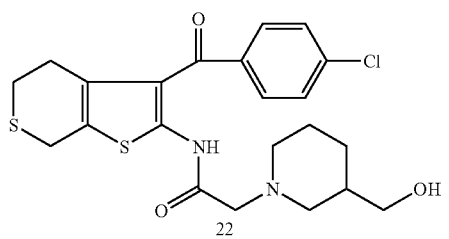
22
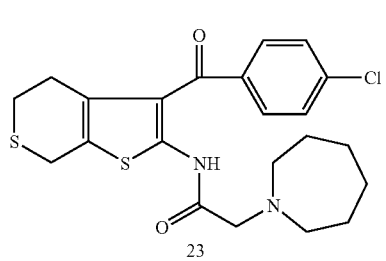
23
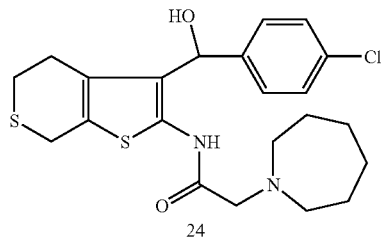
24

TABLE 1-continued
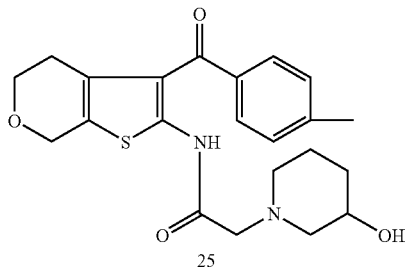
25
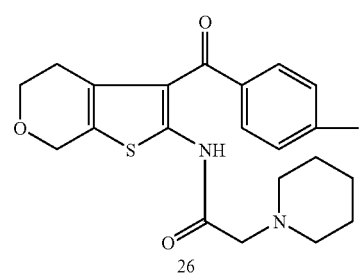
26
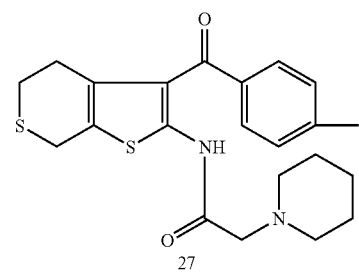
27
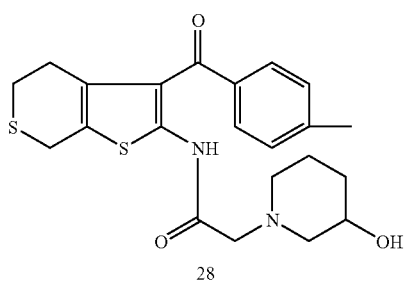
28
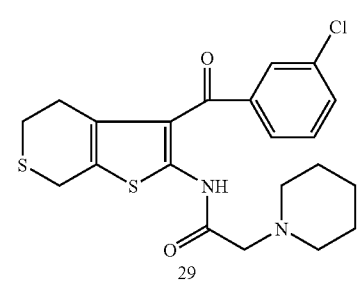
29
TABLE 1-continued
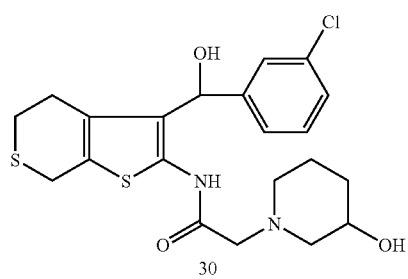
30
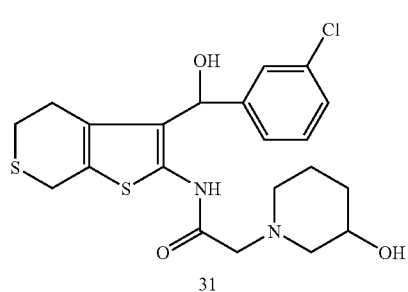
31
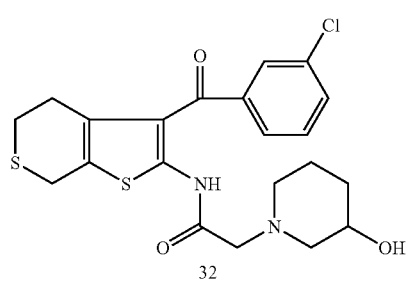
32
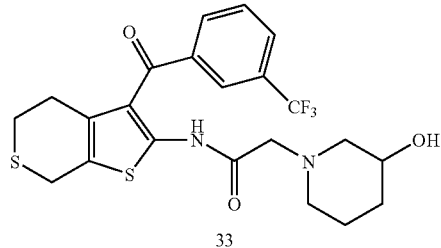
33
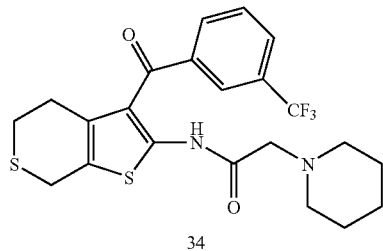
34

TABLE 1-continued
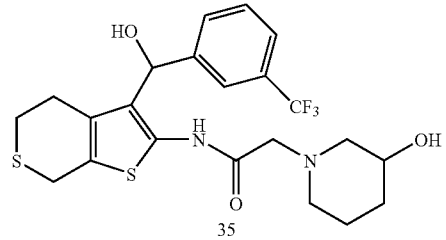
35
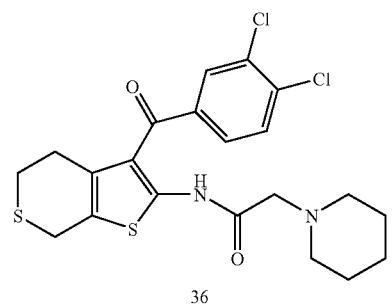
36
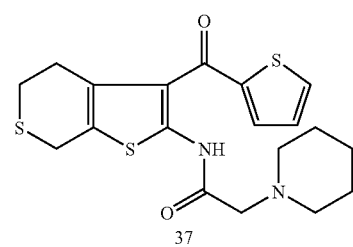
37
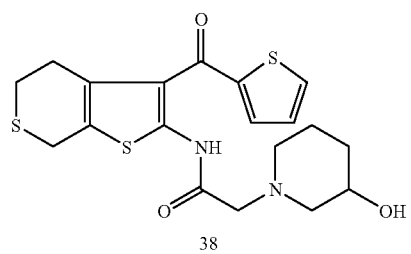
38
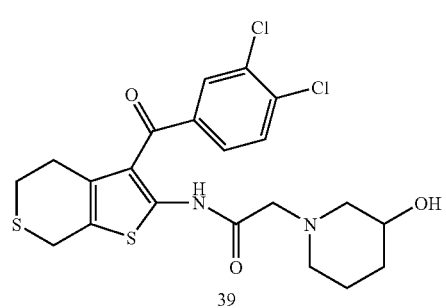
39
TABLE 1-continued
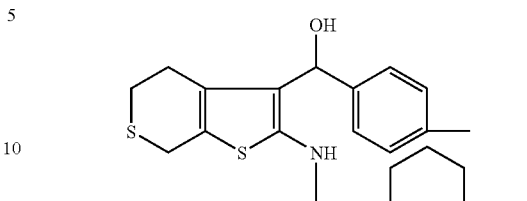
40
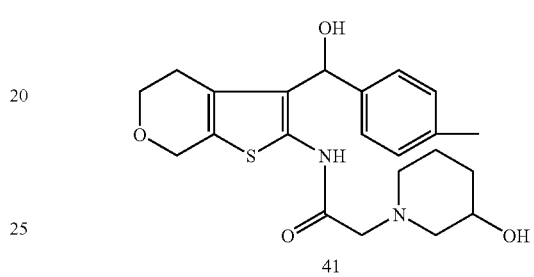
41
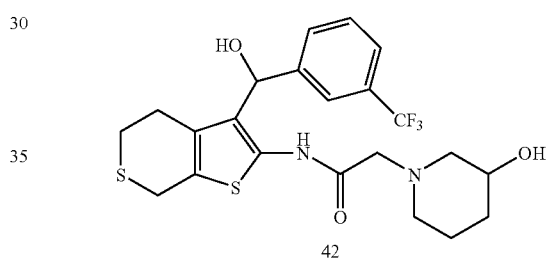
42
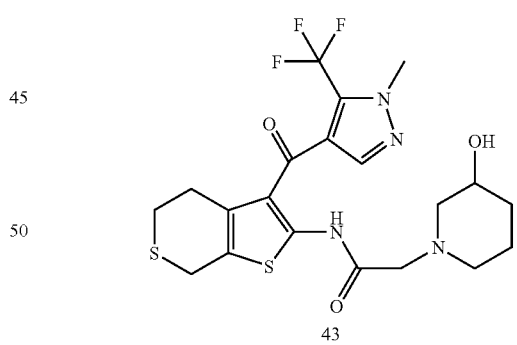
43
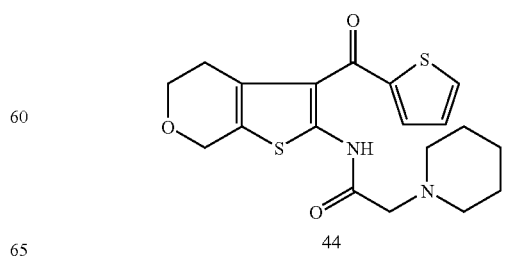
44

TABLE 1-continued
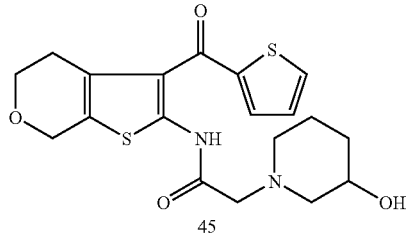
45
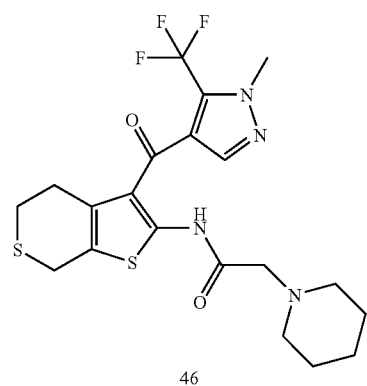
46
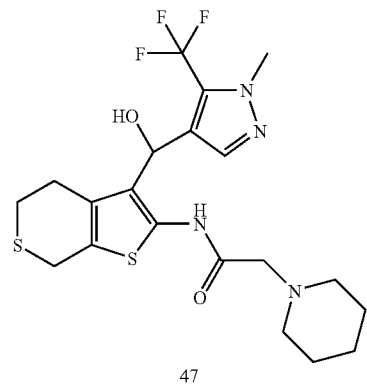
47
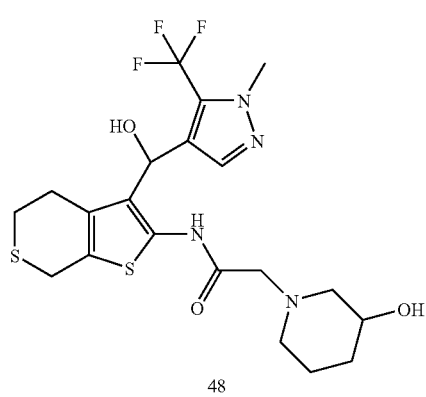
48
TABLE 1-continued
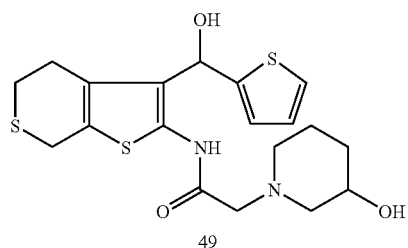
49
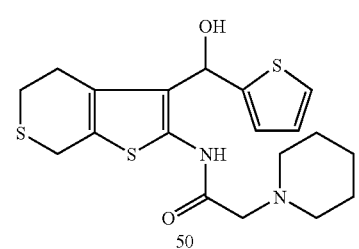
50
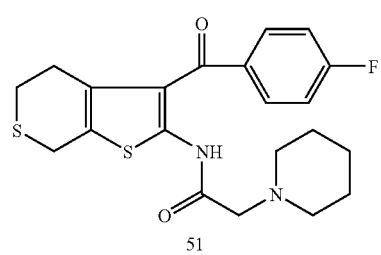
51
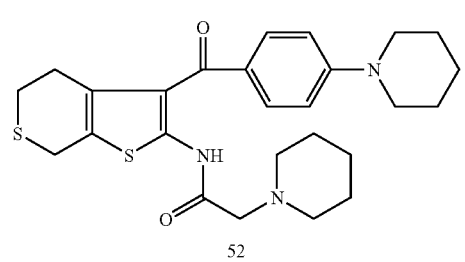
52
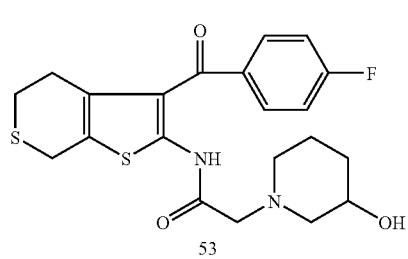
53
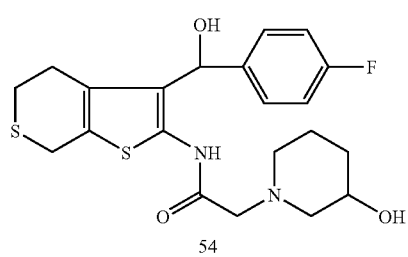
54

TABLE 1-continued
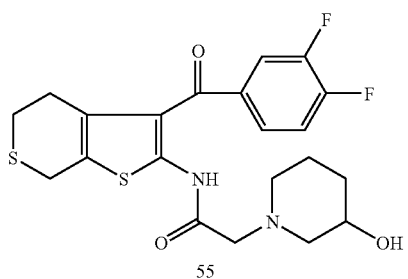
55
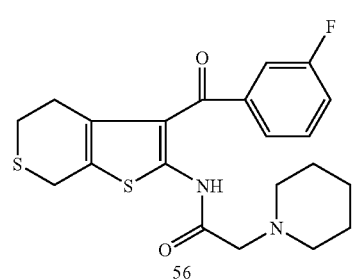
56
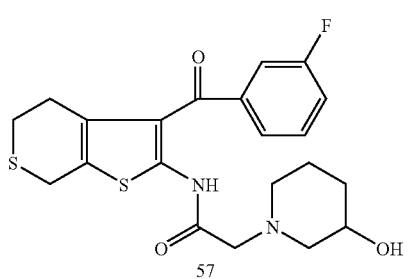
57
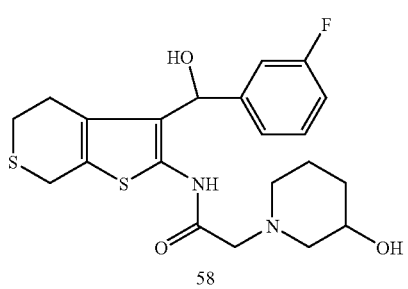
58
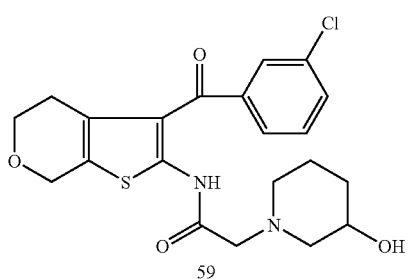
59
TABLE 1-continued
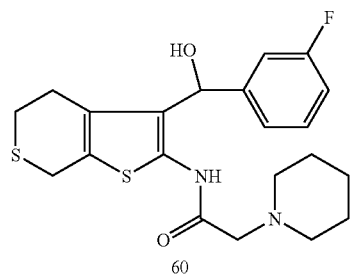
60
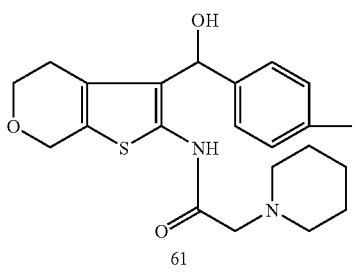
61
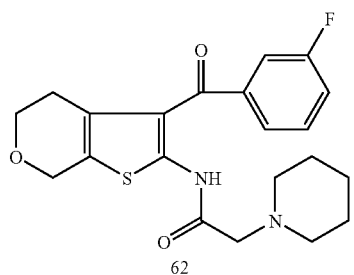
62
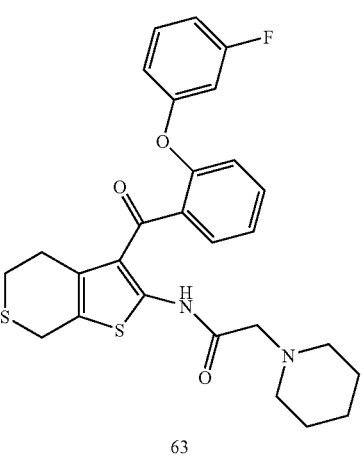
63
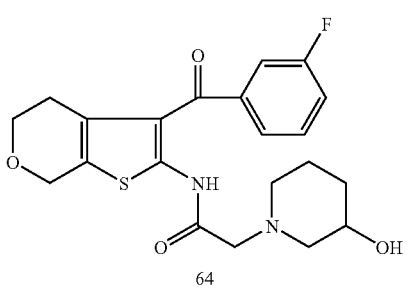
64

TABLE 1-continued
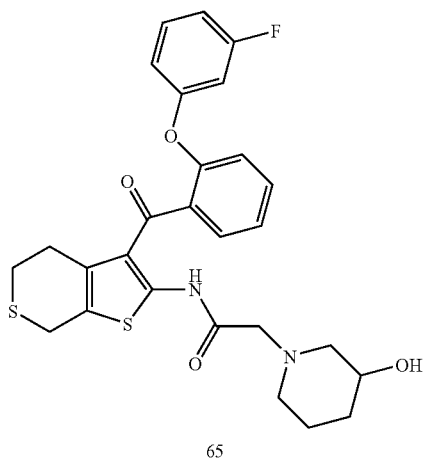
65
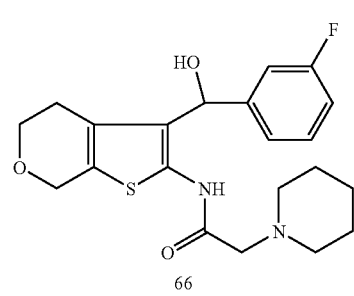
66
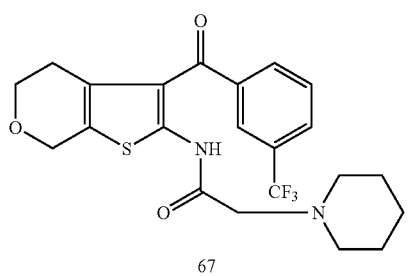
67
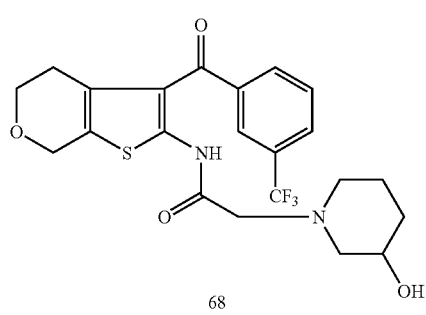
68
TABLE 1-continued
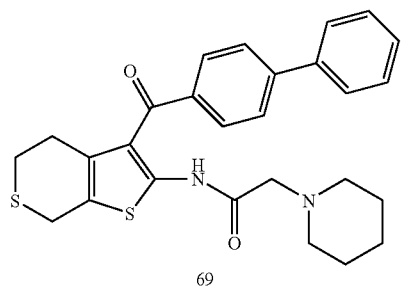
69
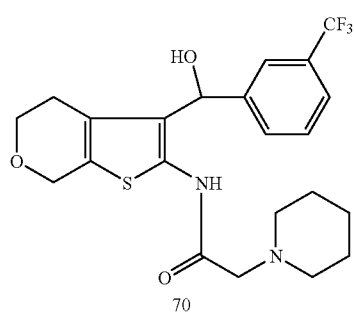
70
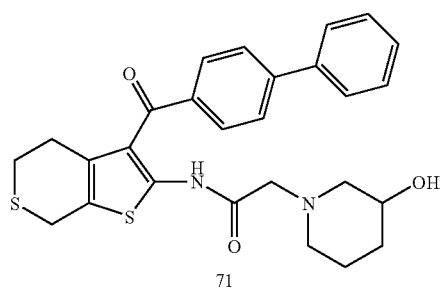
71
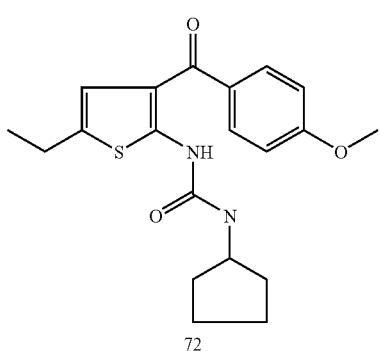
72
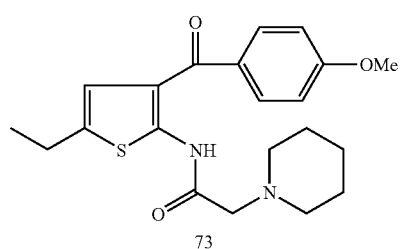
73

TABLE 1-continued

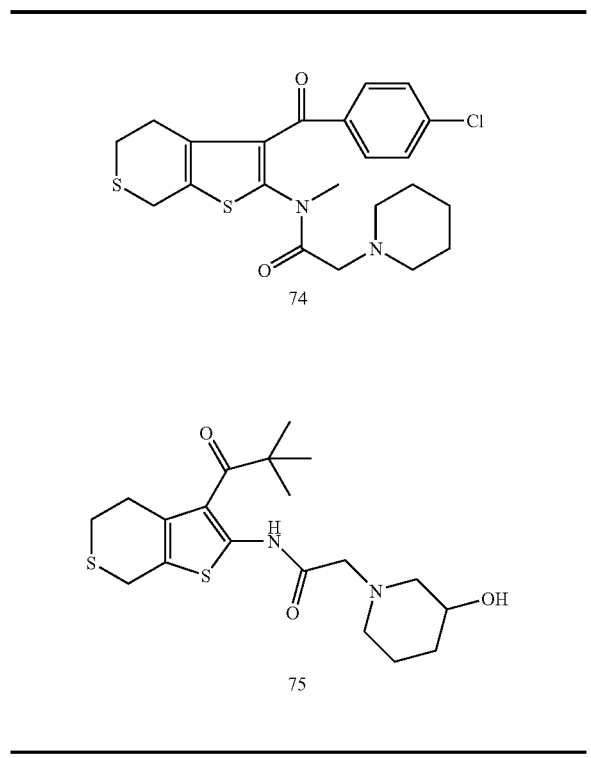

74

75

The following general synthetic sequence is useful in making componds of the present invention.

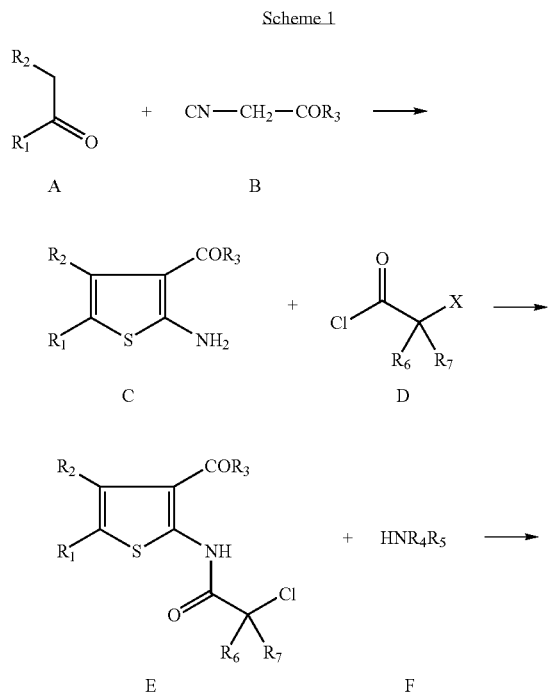

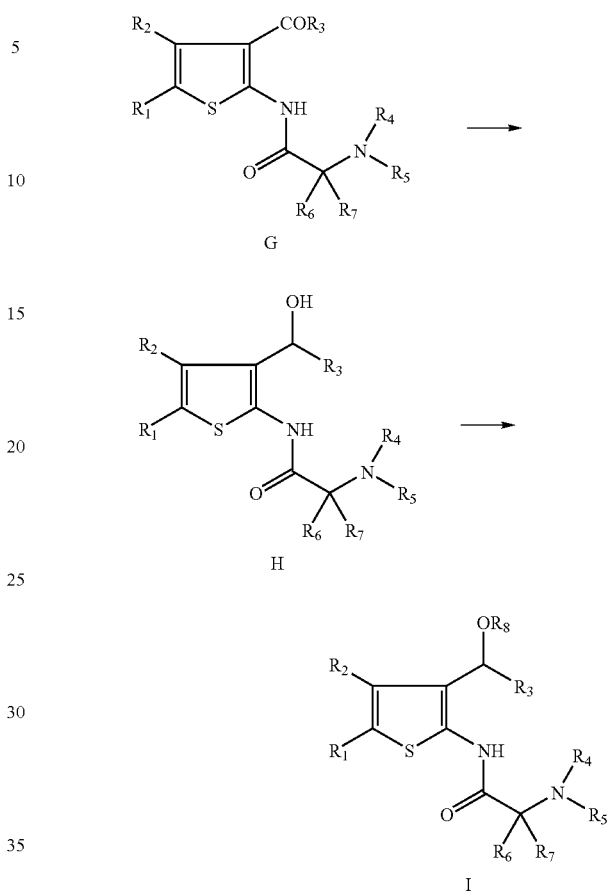

In Scheme 1, ketone A is treated with B and sulfur in the presence of a tertiary organic base such as triethylamine, diisopropylethyl amine, pyridine and the like in a suitable solvent such as DMF and DMSO to give thiophene derivative C according to similar procedures previously described (Perrissin, M., et al., *Eur. J. Med. Chem.—Chim. Ther.*, (1980), 15(5), 413–18. Compound C is treated with an acid chloride derivative D, wherein X is chloro, bromo or iodo, in the presence of a suitable tertiary organic base to give E. Reaction of E with a secondary amine of Formula F in the presence of a suitable tertiary organic base such as triethylamine, diisopropylethyl amine, pyridine and the like gives G. $R_4$ and $R_5$ are independently chosen from $C_1$–$C_6$ alkyl, substituted alkyl, or may be joined together to form a 3- to 8-membered substituted or unsubstituted carbocyclic ring. Compound G is reduced with a suitable hydride reagent such as sodium borohydride and lithium borohydride to give H. Alkylation of H with an akyl halide, methane sulfonate, toluenesulfonate, trifluromethanesulfonate and the like in the presence of a suitable base such as potassium carbonate, lithium hydroxide, and the like produces I.

The invention is described in greater detail by the following non-limiting examples.

EXAMPLE 1

Preparation of 6

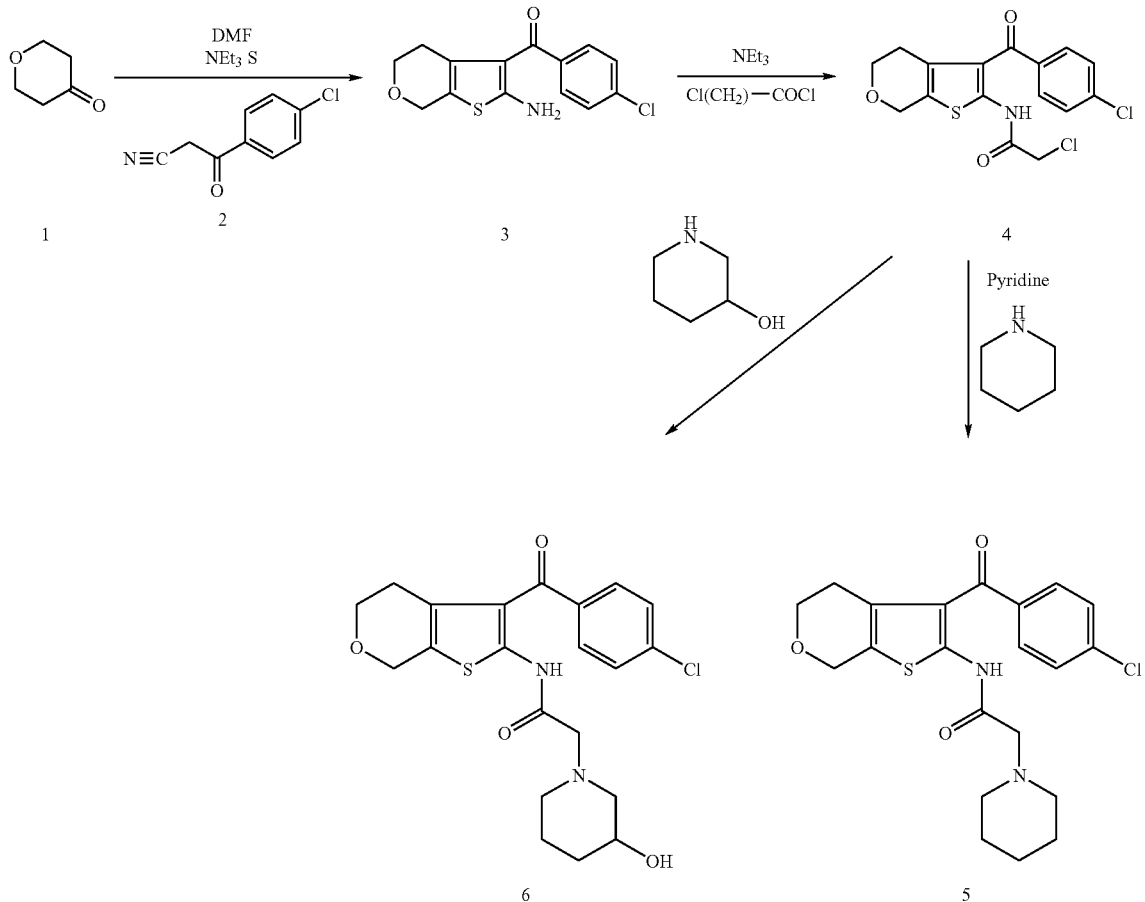

a) Preparation of 3 from 1

To 4-chlorobenzoylacetonitrile (2, 360 mg, 2 mmol) and sulfur (76 mg) in DMF (4 mL), triethylamine, 0.25 mL) is added under stirring. To this mixture tetrahydro-4H-pyran-4-one (1, 200 mg, 2 mmol) is added dropwise. The mixture is stirred for 16 hours and poured into water (30 mL) then extracted with diethyl ether (30 mL). The ethereal solution is dried with sodium sulfate and concentrated to give the desired compound as an orange solid (250 mg, 43%). Physical characteristics: MS (ES+) for m/z 294, 296 (M+H).

b) Preparation of 4 from 3

Compound 3 (224 mg, 0.76 mmol) is dissolved in methylene chloride (15 mL) and treated with triethyl amine (0.42 mL, 3.0 mmol). To this mixture, chloroacetyl chloride (0.18 mL, 2.29 mmol) dissolved in diethyl ether (3 mL) is added dropwise at room temperature. This mixture is stirred for 2 hours at room temperature. Insoluble material is filtered off and the filtrate is concentrated. The mixture is partitioned between water (20 mL) and methylene chloride (20 mL). The organic layer is separated, dried (MgSO$_4$) and concentrated. The residue is triturated with MeOH and the precipitate is filtered and dried to give the desired product as a brown solid (200 mg, 71% yield). Physical characteristics: MS (ES−) for m/z 368, 370 (M−H).

c) Preparation of 5

Compound 3 (47 mg, 0.13 mmol) is dissolved in pyridine (1 mL) and treated with piperidine (43 mg, 0.5 mmol). The mixture is heated to 80° C. for 2 hours. After pyridine is removed the residue is chromatographed on a silica plate by elution with 33% ethyl acetate in hexanes. The desired compound is isolated as a pale yellow solid (40 mg, 75% yield). Physical characteristics: MS (ES+) for m/z 419, 421 (M+H)$^+$; $^1$H NMR (CDCl$_3$) δ 12.3, 7,56, 7.44, 4.74, 3.71, 3.19, 2.53, 2.10, 1.72, 1,26.

d) Preparation of 6

Compound 3 (50 mg, 0.14 mmol) is dissolved in pyridine (1 mL) and treated with 3-hydroxypiperidine (40 mg, 0.4 mmol). The mixture is heated to 80° C. for 2 hours. After pyridine is removed the residue is chromatographed on a silica plate by elution with 50% ethyl acetate in hexanes. The desired compound is isolated as a pale yellow solid (40 mg, 68% yield). Physical characteristics: MS (ES+) for m/z 435, 437 (M+H); $^1$H NMR (CDCl$_3$) δ 12.6, 7.54, 7.44, 4.74, 3.96, 3.72, 3.23, 2.6–2.8, 2.41, 2.0–2.2, 1.5–1.8.

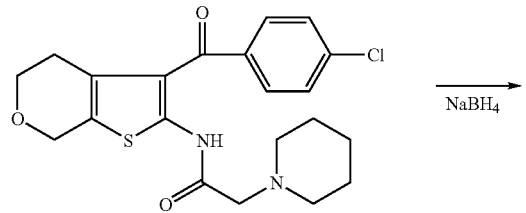

EXAMPLE 2

Preparation of 7

Compound 5 (25 mg, 0.06 mmol) is dissolved in MeOH (5 mL) and treated with sodium borohydride (5 mg) at room temperature for 1 hour. The mixture is taken in ethyl acetate (15 mL) and washed with 5% aqueous solution of NaHCO$_3$. The organic layer is separated, dried (MgSO$_4$) and concentrated to give 7 as a white solid (20 mg, 80%). Physical characteristics: MS (ES+) for m/z 421, 423 (M+H); $^1$H NMR (CD$_3$OD) δ 7.30, 5.83, 4.72, 3.91, 3.20, 2.50, 2.2–2.3, 1.59, 1.27.

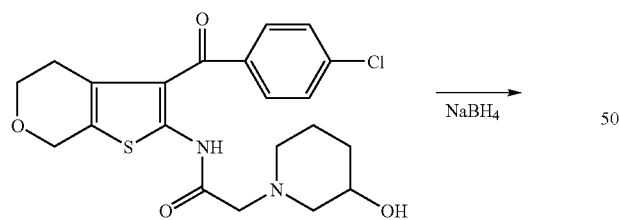

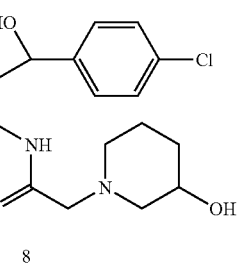

EXAMPLE 3

Preparation of 8

Compound 6 (25 mg, 0.06 mmol) is dissolved in MeOH (5 mL) and treated with sodium borohydride (5 mg) at room temperature for 1 hour. The mixture is taken in ethyl acetate (15 mL) and washed with 5% aqueous solution of NaHCO$_3$. The organic layer is separated, dried (MgSO$_4$) and concentrated to give 8 as a white solid (18 mg, 72%). Physical characteristics: MS (ES+) for m/z 437, 439 (M+H)$^+$; $^1$H NMR(CDCl$_3$) δ 11.2, 11.1, 7.27, 7.21, 5.84, 4.71, 3.86, 3.75, 3.71, 3.0–3.1, 2.1–2.7, 1.78, 1.2–1.6.

EXAMPLE 4

Preparation of 10

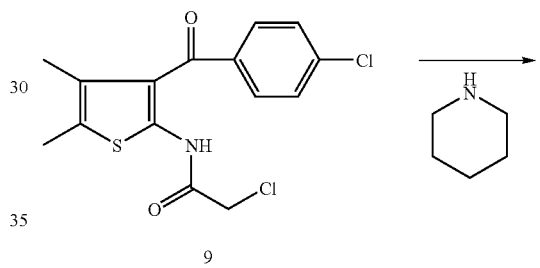

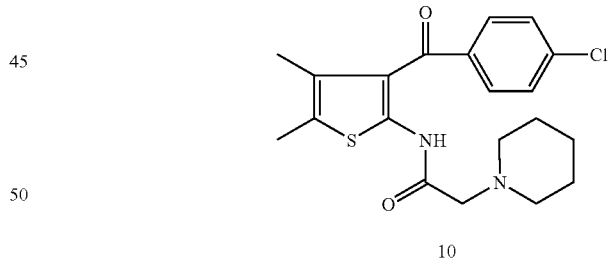

Compound 9 (25 mg, 0.09 mmol) is dissolved in pyridine (1 mL) and treated with piperidine (43 mg, 0.5 mmol). The mixture is heated to 80° C. for 2 hours. After pyridine is removed the residue is chromatographed on a silica plate by elution with 20% ethyl acetate in hexanes. The desired compound is isolated as a pale yellow solid (28 mg, 82% yield). Physical characteristics: MS (ES+) for m/z 391, 393 (M+H)$^+$; $^1$H NMR (CDCl$_3$) δ 11.8, 7.59, 7.43, 3.14, 2.49, 2.26, 1.6–1.8, 1.25.

EXAMPLE 5

Preparation of 14

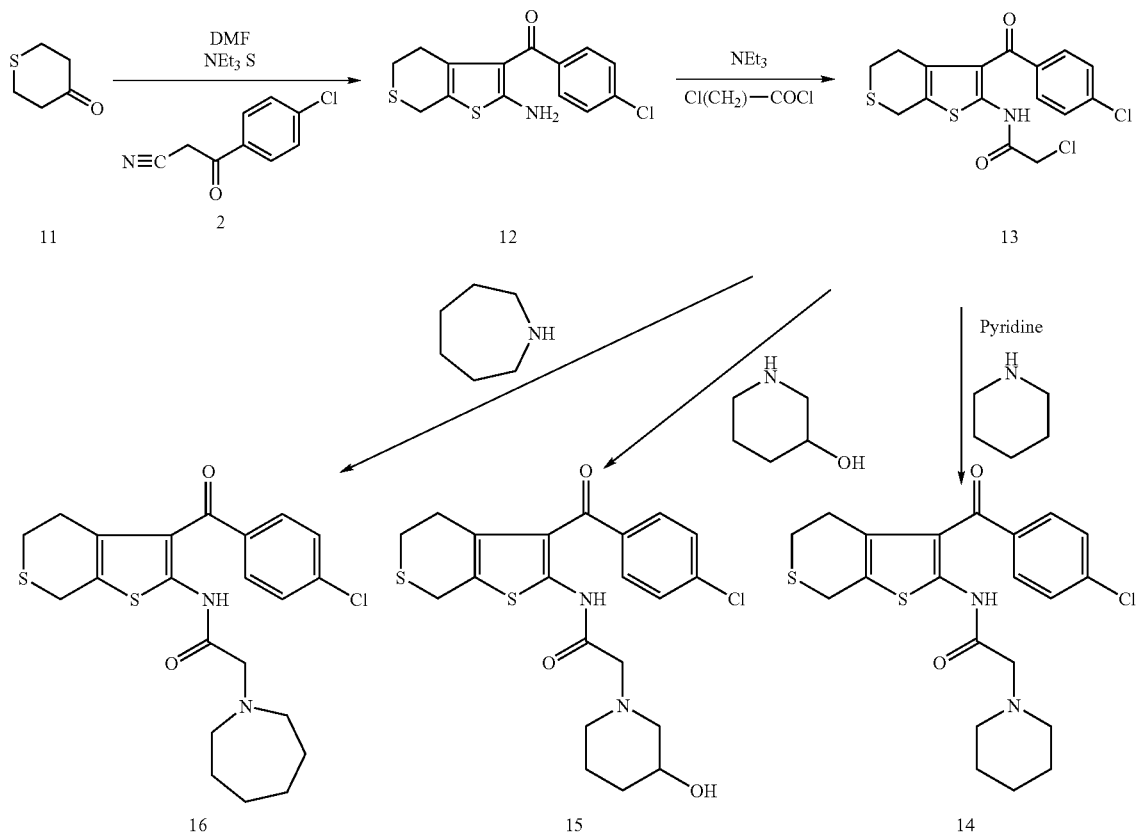

a) Preparation of 12

To 4-chlorobenzoylacetonitrile (2, 3.6 g, 20 mmol) and sulfur (0.65 g) in DMF (6 mL), triethylamine (2.0 mL) is added under stirring. To this solution tetrahydrothiopyran-4-one (11, 2.32 g, 20 mmol) is added dropwise. The mixture is heated to 65° C. for 2 hours and it is poured into water (60 mL), which is extracted with diethyl ether (50 mL). The ethereal solution is dried with sodium sulfate and concentrated to give the desired compound as a brown solid (5.07 g, 82% yield). Physical characteristics: MS (ES+) for m/z 310.

b) Preparation of 13

Compound 11 (1.3 g, 4.2 mmol) is dissolved in diethyl ether (60 mL) and treated with triethyl amine (0.7 mL). To this mixture, chloroacetyl chloride (0.72 mL) dissolved in diethyl ether (5 mL) is added dropwise at room temperature. This mixture is stirred for 5 hours at room temperature. The mixture is partitioned between water (30 mL) and ethyl acetate (30 mL). The organic layer is separated, dried (MgSO$_4$) and concentrated. The residue is triturated with MeOH and the precipitate is filtered and dried to give the desired product as a brown solid (1.14 g, 70% yield). Physical characteristics: MS (ES−) for m/z 384 (M−H).

c) Preparation of 14

Compound 13 (0.4 g, 1.04 mmol) is dissolved in pyridine (5 mL) and treated with piperidine (103 mg, 1.18 mmol). The mixture is heated to 80° C. for 2 hours. After pyridine is removed the residue is chromatographed on a silica plate by elution with 10% ethyl acetate in heptane. The desired compound is isolated as a yellow solid (0.18 g, 40% yield).

Physical characteristics: MS (ES+) for m/z 435, 437 (M+H); $^1$H NMR(CDCl$_3$) δ 11.9, 7.62, 7.46, 3.81, 3.18, 2.67, 2.52, 2.35, 1.70, 1.49.

EXAMPLE 6

Preparation of 15

Compound 13 (0.35 g, 0.91 mmol) is dissolved in pyridine (6 mL) and treated with 3-hydroxypiperidine (100 mg, 1.03 mmol). The mixture is heated to 80° C. for 2 hours. After pyridine is removed the residue is chromatographed on a silica plate by elution with 33% ethyl acetate in heptane. The desired compound is isolated as a white solid (0.14 g, 34% yield). Physical characteristics: MS (ES+) for m/z 451, 453 (M+H); $^1$H NMR (CDCl$_3$) δ 12.5, 7.60, 7.45, 3.98, 3.81, 2.6–2.8, 2.42, 2.33, 2.05, 1.3–1.8.

EXAMPLE 7

Preparation of 16

Compound 13 (88 mg, 0.22 mmol) is dissolved in pyridine (2 mL) and treated with hexamethyleneimine (60 mg, 0.6 mmol). The mixture is heated to 80° C. for 2 hours. After pyridine is removed the residue is chromatographed on a silica plate by elution with 20% ethyl acetate in hexane. The desired compound is isolated as a yellow solid (77 mg, 78% yield). Physical characteristics: MS (ES+) for m/z 449, 451 (M+H); ¹H NMR (CDCl₃) δ 11.8, 7.60, 7.44, 3.79, 3.33, 2.72, 2.66, 2.35, 1.67, 1.59.

EXAMPLE 8

Preparation of 17

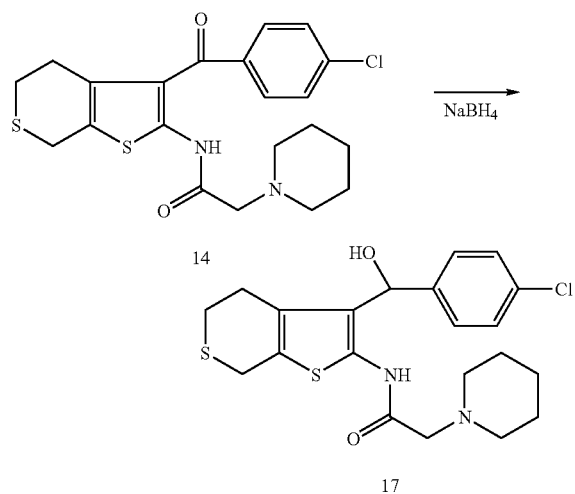

Compound 14 (33 mg, 0.076 mmol) is dissolved in MeOH (5 mL) and treated with sodium borohydride (5 mg) at room temperature for 1 hour. The mixture is taken in ethyl acetate (15 mL) and washed with 5% aqueous solution of NaHCO₃. The organic layer is separated, dried (MgSO₄) and concentrated to give 17 as a white solid (25 mg, 76%). Physical characteristics: MS (ES+) for m/z 437, 439 (M+H); ¹H NMR (CDCl₃) δ 10.7, 7.29, 5.87, 3.75, 3.02, 2.86, 2.4–2.7, 1.3–1.6.

EXAMPLE 9

Preparation of 18

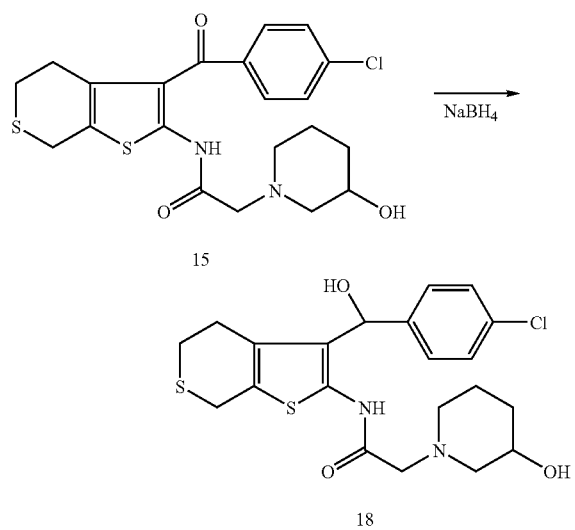

Compound 15 (28 mg, 0.066 mmol) is dissolved in MeOH (5 mL) and treated with sodium borohydride (5 mg) at room temperature for 1 hour. The mixture is taken in ethyl acetate (15 mL) and washed with 5% aqueous solution of NaHCO₃. The organic layer is separated, dried (MgSO₄) and concentrated. The residue is subjected to chromatography to separate the diastereomers by elution with 5% MeOH in methylene chloride. Compound 18 is isolated as a white solid (10 mg, 36%). Physical characteristics: MS (ES+) for m/z 453, 455 (M+H); ¹H NMR (CDCl₃) δ 11.2, 7.26, 7.20, 5.84, 3.74, 3.06, 3.01, 2.80, 2.5–2.8, 2.31, 1.2–1.9.

EXAMPLE 10

Preparation of 19

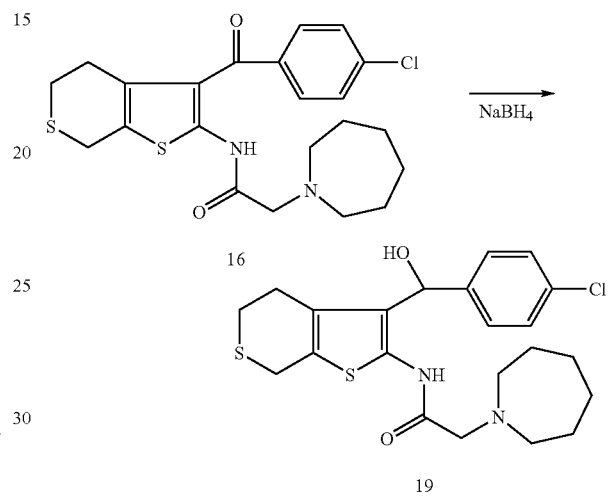

Compound 16 (50 mg, 0.076 mmol) is dissolved in MeOH (10 mL) and treated with sodium borohydride (10 mg) at room temperature for 1 hour. The mixture is taken in ethyl acetate (20 mL) and washed with 5% aqueous solution of NaHCO₃. The organic layer is separated, dried (MgSO₄) and concentrated to give 19 as a white solid (35 mg, 70%). Physical characteristics: MS (ES+) for m/z 451, 453 (M+H); ¹H NMR (CDCl₃) δ 10.7, 7.29, 7.25, 5.87, 3.75, 3.17, 2.5–2.9, 1.5–1.8.

EXAMPLE 11

Preparation of 23

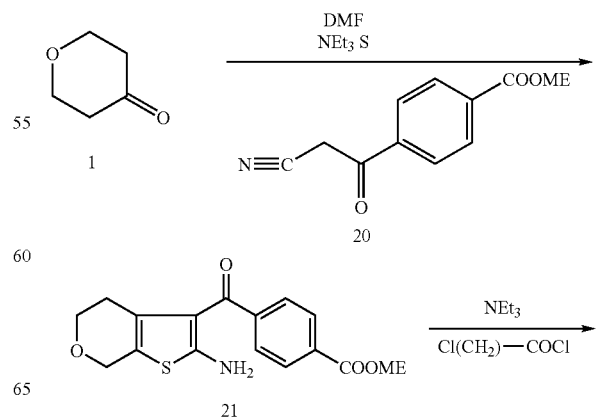

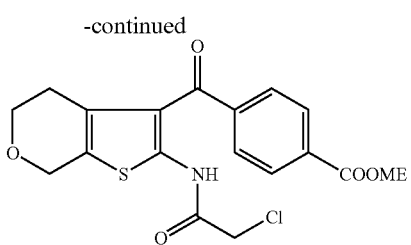

22

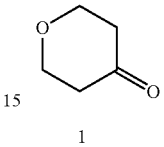

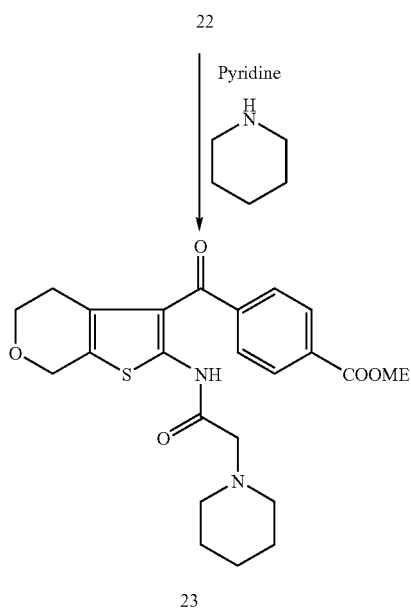

23 a) Preparation of 21 from 1

To 4-carbomethoxybenzoylacetonitrile (20, 406 mg, 2 mmol) and sulfur (76 mg) in DMF (4 mL), triethylamine, 0.25 mL) is added under stirring. To this solution tetrahydro-4H-pyran-4-one (1, 200 mg, 2 mmol) is added dropwise. The mixture is stirred for 16 hours and it is poured into water (30 mL), which is extracted with diethyl ether (30 mL). The ethereal solution is dried with sodium sulfate and concentrated to give the desired compound as an orange solid (475 mg, 75%). Physical characteristics: MS (ES+) for m/z 318 (M+H).

b) Preparation of 22

Compound 21 (300 mg, 0.95 mmol) is dissolved in methylene chloride (20 mL) and treated with triethyl amine (0.5 mL, 3.6 mmol). To this mixture, chloroacetyl chloride (0.25 mL, 3.18 mmol) dissolved in diethyl ether (4 mL) is added dropwise at room temperature. This mixture is stirred for 16 hours at room temperature. Insoluble material is filtered off and the filtrate is concentrated. The mixture is partitioned between water (30 mL) and methylene chloride (30 mL). The organic layer is separated, dried (MgSO$_4$) and concentrated. The residue is triturated with MeOH and the precipitate is filtered and dried to give the desired product as a brown solid (210 mg, 56% yield). Physical characteristics: MS (ES–) for m/z 392, 394 (M–H).

c) Preparation of 23

Compound 22 (50 mg, 0.13 mmol) is dissolved in pyridine (2 mL) and treated with piperidine (43 mg, 0.5 mmol). The mixture is heated to 80° C. for 2 hours. After pyridine is removed the residue is chromatographed on a silica plate by elution with 33% ethyl acetate in hexanes. The desired compound is isolated as a pale yellow solid (42 mg, 75% yield). Physical characteristics: MS (ES+) for m/z 465 (M+Na); $^1$H NMR (CDCl$_3$) δ 12.5, 8.13, 7.63, 4.73, 3.96, 3.66, 3.21, 2.55, 1.99, 1.72, 1,48.

EXAMPLE 12

Preparation of 27 from 1

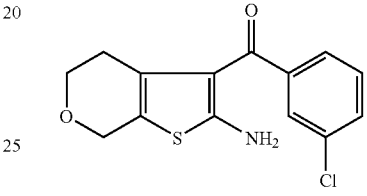

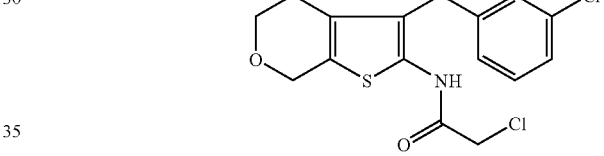

26

27 a) Preparation of 25 from 1

To 3-chlorobenzoylacetonitrile (24, 360 mg, 2 mmol) and sulfur (76 mg) in DMF (4 mL), triethylamine (0.25 mL) is added under stirring. To this solution tetrahydro-4H-pyran-4-one (1, 200 mg, 2 mmol) is added dropwise. The mixture is stirred for 16 hours and it is poured into water (30 mL), which is extracted with diethyl ether (30 mL). The ethereal solution is dried with sodium sulfate and concentrated to give the desired compound as an orange solid (253 mg, 43%). Physical characteristics: MS (ES+) for m/z 294, 296 (M+H).

b) Preparation of 26 from 25

(M+H); $^1$H NMR (CDCl$_3$) δ 12.5, 7.3–7.7, 4.74, 3.70, 3.20, 2.54, 2.07, 1.73, 1.49.

EXAMPLE 13

Preparation of 30

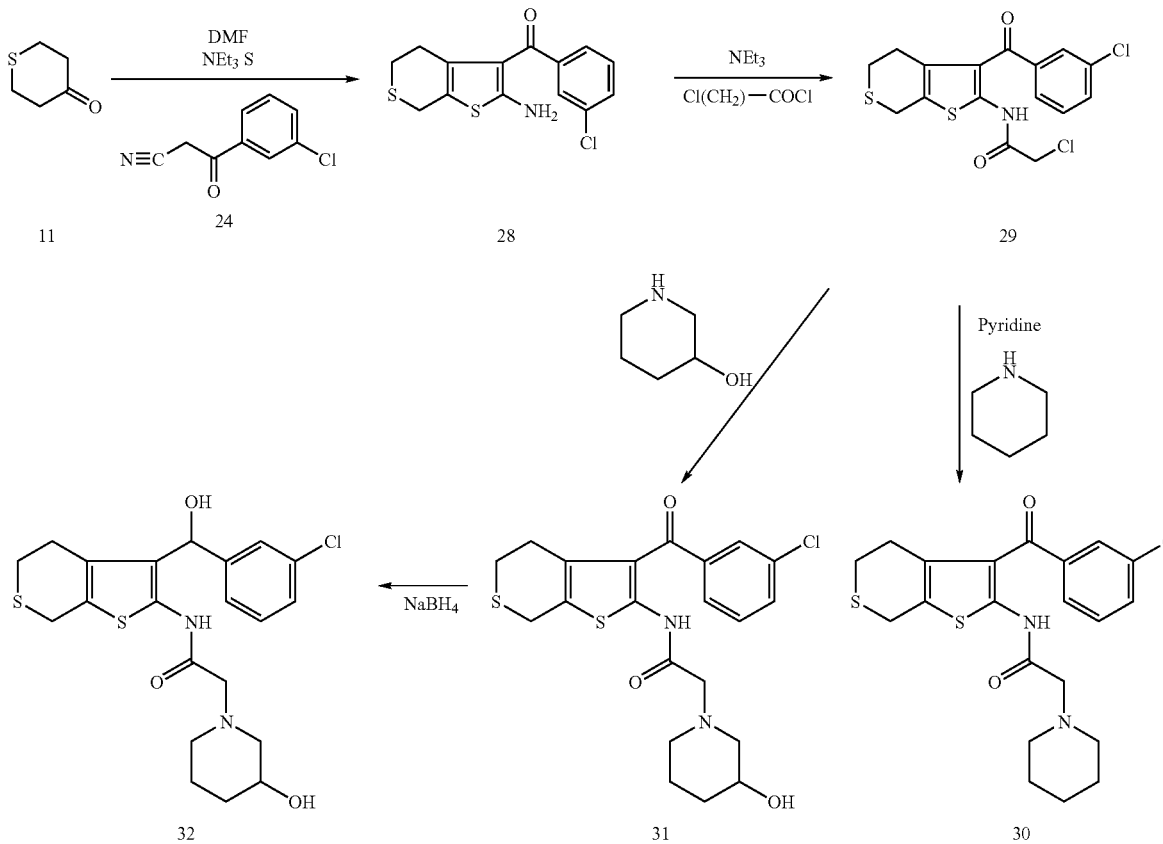

Compound 25 (253 mg, 0.86 mmol) is dissolved in methylene chloride (15 mL) and treated with triethyl amine (0.5 mL, 3.6 mmol). To this mixture, chloroacetyl chloride (0.2 mL, 2.58 mmol) dissolved in diethyl ether (3 mL) is added dropwise at room temperature. This mixture is stirred for 16 hours at room temperature. Insoluble material is filtered off and the filtrate is concentrated. The mixture is partitioned between water (30 mL) and methylene chloride (30 mL). The organic layer is separated, dried (MgSO$_4$) and concentrated. The residue is triturated with MeOH and the precipitate is filtered and dried to give the desired product as a brown solid (210 mg, 66% yield). Physical characteristics: MS (ES−) for m/z 368, 370 (M−H).

c) Preparation of 27

Compound 26 (50 mg, 0.13 mmol) is dissolved in pyridine (2 mL) and treated with piperidine (43 mg, 0.5 mmol). The mixture is heated to 80° C. for 2 hours. After pyridine is removed the residue is chromatographed on a silica plate by elution with 33% ethyl acetate in hexanes. The desired compound is isolated as a pale yellow solid (35 mg, 61% yield). Physical characteristics: MS (ES+) for m/z 419, 421 a) Preparation of 28 from 11

To 3-chlorobenzoylacetonitrile (24, 360 mg, 2 mmol) and sulfur (76 mg) in DMF (4 mL), triethylamine (0.25 mL) is added under stirring. To this solution tetrahydrothiopyran-4-one (11, 232 mg, 2 mmol) is added dropwise. The mixture is stirred for 16 hours and it is poured into water (30 mL), which is extracted with diethyl ether (30 mL). The ethereal solution is dried with sodium sulfate and concentrated to give the desired compound as an orange solid (373 mg, 78%). Physical characteristics: MS (ES+) for m/z 294, 296 (M+H).

b) Preparation of 29 from 28

Compound 28 (373 mg, 1.27 mmol) is dissolved in methylene chloride (15 mL) and treated with triethyl amine (0.75 mL, 5.4 mmol). To this mixture, chloroacetyl chloride (0.3 mL, 3.87 mmol) dissolved in diethyl ether (3 mL) is added dropwise at room temperature. This mixture is stirred for 16 hours at room temperature. Insoluble material is filtered off and the filtrate is concentrated. The mixture is partitioned between water (30 mL) and methylene chloride (30 mL). The organic layer is separated, dried (MgSO$_4$) and concentrated. The residue is subjected to chromatography by elution with 25% ethyl acetate in hexanes to give the desired product as a pale yellow solid (230 mg, 47% yield). Physical characteristics: MS (ES−) for m/z 384, 386 (M−H).

c) Preparation of 30

Compound 29 (50 mg, 0.13 mmol) is dissolved in pyridine (2 mL) and treated with piperidine (43 mg, 0.5 mmol). The mixture is heated to 80° C. for 2 hours. After pyridine is removed the residue is chromatographed on a silica plate by elution with 20% ethyl acetate in hexanes. The desired compound is isolated as a pale yellow solid (20 mg, 36% yield). Physical characteristics: MS (ES+) for m/z 435, 437 (M+H)+; $^1$H NMR(CDCl$_3$) δ 12.1, 7.3–7.7, 3.79, 3.17, 2.64, 2.51, 2.30, 1.70, 1.47.

EXAMPLE 14

Preparation of 31

Compound 29 (100 mg, 0.26 mmol) is dissolved in pyridine (4 mL) and treated with 3-hydroxypiperidine (100 mg, 1.03 mmol). The mixture is heated to 80° C. for 2 hours. After pyridine is removed the residue is chromatographed on a silica plate by elution with 67% ethyl acetate in hexanes. The desired compound is isolated as a pale yellow solid (82 mg, 70% yield). Physical characteristics: MS (ES+) for m/z 451, 453 (M+H); $^1$H NMR(CDCl$_3$) δ 12.5, 7.3–7.7, 4.74, 3.95, 3.79, 3.21, 2.6–2.9, 2.41, 2.28, 2.04, 1.5–1.8.

EXAMPLE 15

Preparation of 32

Compound 31 (60 mg, 0.133 mmol) is dissolved in MeOH (10 mL) and treated with sodium borohydride (10 mg) at room temperature for 1 hour. The mixture is taken in ethyl acetate (20 mL) and washed with 5% aqueous solution of NaHCO$_3$. The organic layer is separated, dried (MgSO$_4$) and concentrated. The residue is subjected to chromatography by elution with 5% MeOH in methylene chloride to give 32 as a pale yellow solid (27 mg, 45%). Physical characteristics: MS (ES+) for m/z 453, 455 (M+H); $^1$H NMR (CDCl$_3$) δ 11.2, 7.1–7.4, 5.81, 3.74, 3.05, 2.84, 2.3–2.7, 1.73, 1.58, 1.44.

EXAMPLE 16

Preparation of 36

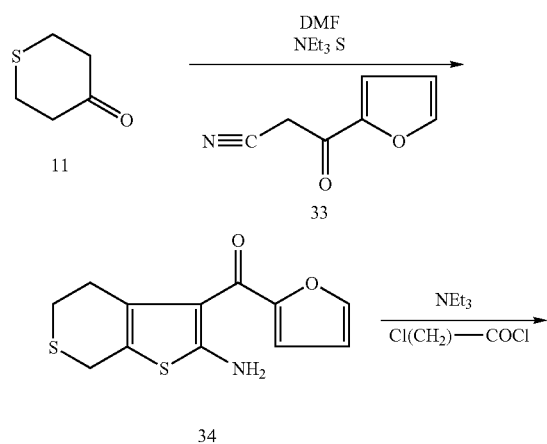

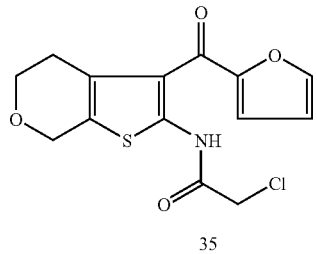

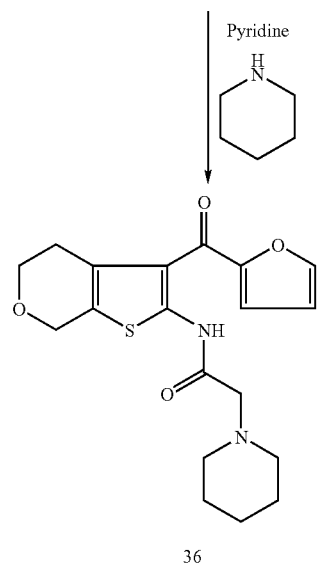

a) Preparation of 34

To 2-furoylacetonitirle (33, 2.71 g, 20 mmol) and sulfur (0.49 g) in DMF (5 mL), triethylamine (1.5 mL) is added under stirring. To this solution tetrahydrothiopyran-4-one (11, 2.0 g, 17 mmol) is added. The mixture is heated to 65° C. for 2 hours and it is poured into water (60 mL), which is extracted with ethyl acetate (50 mL). The organic solution is dried with sodium sulfate and concentrated to give the desired compound as a brown solid (2.55 g, 57% yield). Physical characteristics: MS (ES+) for m/z 266 (M+H).

b) Preparation of 35

Compound 34 (1.0 g, 3.8 mmol) is dissolved in diethyl ether (60 mL) and treated with triethyl amine (0.6 mL). To this mixture, chloroacetyl chloride (0.53 mL) dissolved in diethyl ether (5 mL) is added dropwise at room temperature. This mixture is stirred for 5 hours at room temperature. The mixture is partitioned between water (30 mL) and ethyl acetate (30 mL). The organic layer is separated, dried (MgSO$_4$) and concentrated. The residue is triturated with MeOH and the precipitate is filtered and dried to give the desired product as a brown solid (1.02 g, 79% yield). Physical characteristics: MS (ES−) for m/z 340, 342 (M−H).

c) Preparation of 36

Compound 35 (0.35 g, 1.03 mmol) is dissolved in pyridine (5 mL) and treated with piperidine (103 mg, 1.18 mmol). The mixture is heated to 80° C. for 2 hours. After pyridine is removed the residue is chroratographed on a silica plate by elution with 20% ethyl acetate in heptane. The desired compound is isolated as a yellow solid (0.058 g, 14% yield). Physical characteristics: MS (ES+) for m/z 391 (M+H); $^1$H NMR (CDCl$_3$) δ 11.5, 7.67, 7.19, 6.61, 3.84, 3.15, 2.75, 2.51, 1.5–1.8.

EXAMPLE 17

Further Non-Limiting Examples

N-[3-(4-chlorobenzoyl)-4,7-dihydro-5H-thieno[2,3-c]pyran-2-yl]-2-piperidin-1-ylacetamide;
N-{3-[(4-chlorophenyl)(hydroxy)methyl]-4,7-dihydro-5H-thieno[2,3-c]pyran-2-yl}-2-piperidin-1-ylacetamide;
N-[3-(4-chlorobenzoyl)-4,7-dihydro-5H-thieno[2,3-c]pyran-2-yl]-2-(3-hydroxypiperidin-1-yl)acetamide;
N-{3-[(4-chlorophenyl)(hydroxy)methyl]-4,7-dihydro-5H-thieno[2,3-c]pyran-2-yl}-2-(3-hydroxypiperidin-1-yl)acetamide;
N-[5-ethyl-3-(4-methoxybenzoyl)thien-2-yl]-2-piperidin-1-ylacetamide; N-[5-ethyl-3-(4-methoxybenzoyl)thien-2-yl]-2-pyrrolidin-1-ylacetamide;
N-[4-methyl-3-(benzoyl)thien-2-yl]-2-piperidin-1-ylacetamide;
N-[4,5-dimethyl-3-(4-chlorobenzoyl)thien-2-yl]-2-piperidin-1-ylacetamide;
N-[3-(4-chlorobenzoyl)-4,7-dihydro-5H-thieno[2,3-c]thiopyran-2-yl]-2-piperidin-1-ylacetamide;
N-[3-(4-chlorobenzoyl)-4,7-dihydro-5H-thieno[2,3-c]thiopyran-2-yl]-2-(3-hydroxypiperidin-1-yl)acetamide;
N-[3-(2-furoyl)-4,7-dihydro-5H-thieno[2,3-c]thiopyran-2-yl]-2-piperidin-1-ylacetamide;
N-[3-(2-furoyl)-4,7-dihydro-5H-thieno[2,3-c]thiopyran-2-yl]-2-(3-hydroxypiperidin-1-yl)acetamide;
methyl 4-({2-[(piperidin-1-ylacetyl)amino]-4,7-dihydro-5H-thieno[2,3-c]pyran-3-yl}carbonyl)benzoate;
N-[3-(3-chlorobenzoyl)-4,7-dihydro-5H-thieno[2,3-c]pyran-2-yl]-2-piperidin-1-ylacetamide;
N-[3-(2-furoyl)-4,7-dihydro-5H-thieno[2,3-c]pyran-2-yl]-2-piperidin-1-ylacetamide;
N-[3-(2-furoyl)-4,7-dihydro-5H-thieno[2,3-c]pyran-2-yl]-2-(3-hydroxypiperidin-1-yl)acetamide;
N-{3-[(4-chlorophenyl)sulfonyl]thien-2-yl}-2-piperidin-1-ylacetamide;
N-[(2Z,3Z)-3-(4-chlorobenzylidene)-3,4,5,7-tetrahydro-2H-thieno[2,3-c]pyran-2-ylidene]-2-piperidin-1-ylacetamide;
N-{3-[(4-chlorophenyl)(diethylamino)methyl]-4,7-dihydro-5H-thieno[2,3-c]pyran-2-yl}-2-piperidin-1-ylacetamide, dihydrochloride;
N-{3-[(4-chlorophenyl)(hydroxy)methyl]-4,7-dihydro-5H-thieno[2,3-c]thiopyran-2-yl}-2-piperidin-1-ylacetamide;
N-{3-[(4-chlorophenyl)(hydroxy)methyl]-4,7-dihydro-5H-thieno[2,3-c]thiopyran-2-yl}-2-(3-hydroxypiperidin-1-yl)acetamide;
N-{3-[(4-chlorophenyl)(hydroxy)methyl]-4,7-dihydro-5H-thieno[2,3-c]thiopyran-2-yl}-2-(3-hydroxypiperidin-1-yl)acetamide;
N-[3-(4-chlorobenzoyl)-4,7-dihydro-5H-thieno[2,3-c]pyran-2-yl]-2-[3-(hydroxymethyl)piperidin-1-yl]acetamide;
N-[3-(4-chlorobenzoyl)-4,7-dihydro-5H-thieno[2,3-c]thiopyran-2-yl]-2-[3-(hydroxymethyl)piperidin-1-yl]acetamide;
2-azepan-1-yl-N-[3-(4-chlorobenzoyl)-4,7-dihydro-5H-thieno[2,3-c]thiopyran-2-yl]acetamide;
2-azepan-1-yl-N-{3-[(4-chlorophenyl)(hydroxy)methyl]-4,7-dihydro-5H-thieno[2,3-c]thiopyran-2-yl}acetamide;
N-[3-(4-chlorobenzoyl)-4,7-dihydro-5H-thieno[2,3-c]thiopyran-2-yl]-N-methyl-2-piperidin-1-ylacetamide;
2-(3-hydroxypiperidin-1-yl)-N-[3-(4-methylbenzoyl)-4,7-dihydro-5H-thieno[2,3-c]pyran-2-yl]acetamide;
N-[3-(4-methylbenzoyl)-4,7-dihydro-5H-thieno[2,3-c]pyran-2-yl]-2-piperidin-1-ylacetamide;
N-[3-(4-methylbenzoyl)-4,7-dihydro-5H-thieno[2,3-c]thiopyran-2-yl]-2-piperidin-1-ylacetamide;
2-(3-hydroxypiperidin-1-yl)-N-[3-(4-methylbenzoyl)-4,7-dihydro-5H-thieno[2,3-c]thiopyran-2-yl]acetamide;
N-[3-(3-chlorobenzoyl)-4,7-dihydro-5H-thieno[2,3-c]thiopyran-2-yl]-2-piperidin-1-ylacetamide;
N-{3-[(3-chlorophenyl)(hydroxy)methyl]-4,7-dihydro-5H-thieno[2,3-c]thiopyran-2-yl}-2-(3-hydroxypiperidin-1-yl)acetamide;
N-{3-[(3-chlorophenyl)(hydroxy)methyl]-4,7-dihydro-5H-thieno[2,3-c]thiopyran-2-yl}-2-(3-hydroxypiperidin-1-yl)acetamide;
N-[3-(3-chlorobenzoyl)-4,7-dihydro-5H-thieno[2,3-c]thiopyran-2-yl]-2-(3-hydroxypiperidin-1-yl)acetamide;
2-(3-hydroxypiperidin-1-yl)-N-{3-[3-(trifluoromethyl)benzoyl]-4,7-dihydro-5H-thieno[2,3-c]thiopyran-2-yl}acetamide;
2-piperidin-1-yl-N-{3-[3-(trifluoromethyl)benzoyl]-4,7-dihydro-5H-thieno[2,3-c]thiopyran-2-yl}acetamide;
2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
N-[3-(3,4-dichlorobenzoyl)-4,7-dihydro-5H-thieno[2,3-c]thiopyran-2-yl]-2-piperidin-1-ylacetamide;
N-[3-(2,2-dimethylpropanoyl)-4,7-dihydro-5H-thieno[2,3-c]thiopyran-2-yl]-2-(3-hydroxypiperidin-1-yl)acetamide;
2-piperidin-1-yl-N-[3-(thien-2-ylcarbonyl)-4,7-dihydro-5H-thieno[2,3-c]thiopyran-2-yl]acetamide;
2-(3-hydroxypiperidin-1-yl)-N-[3-(thien-2-ylcarbonyl)-4,7-dihydro-5H-thieno[2,3-c]thiopyran-2-yl]acetamide;
N-[3-(3,4-dichlorobenzoyl)-4,7-dihydro-5H-thieno[2,3-c]thiopyran-2-yl]-2-(3-hydroxypiperidin-1-yl)acetamide;
N-{3-[hydroxy(4-methylphenyl)methyl]-4,7-dihydro-5H-thieno[2,3-c]thiopyran-2-yl}-2-(3-hydroxypiperidin-1-yl)acetamide;
N-{3-[hydroxy(4-methylphenyl)methyl]-4,7-dihydro-5H-thieno[2,3-c]pyran-2-yl}-2-(3-hydroxypiperidin-1-yl)acetamide;
2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
2-(3-hydroxypiperidin-1-yl)-N-(3-{[1-methyl-5-(trifluoromethyl)-1H-pyrazol-4-yl]carbonyl}-4,7-dihydro-5H-thieno[2,3-c]pyran-2-yl)acetamide;
2-piperidin-1-yl-N-[3-(thien-2-ylcarbonyl)-4,7-dihydro-5H-thieno[2,3-c]pyran-2-yl]acetamide;
2-(3-hydroxypiperidin-1-yl)-N-[3-(thien-2-ylcarbonyl)-4,7-dihydro-5H-thieno[2,3-c]pyran-2-yl]acetamide;
N-(3-{[1-methyl-5-(trifluoromethyl)-1H-pyrazol-4-yl]carbonyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-(3-hydroxypiperidin-1-yl)acetamide;
2-(3-hydroxypiperidin-1-yl)-N-{3-[hydroxy(thien-2-yl)methyl]-4,7-dihydro-5H-thieno[2,3-c]thiopyran-2-yl}acetamide;
N-{3-[hydroxy(thien-2-yl)methyl]-4,7-dihydro-5H-thieno[2,3-c]thiopyran-2-yl}-2-piperidin-1-ylacetamide;
N-[3-(4-fluorobenzoyl)-4,7-dihydro-5H-thieno[2,3-c]thiopyran-2-yl]-2-piperidin-1-ylacetamide;

2-piperidin-1-yl-N-[3-(4-piperidin-1-ylbenzoyl)-4,7-di-hydro-5H-thieno[2,3-c]thiopyran-2-yl]acetamide;

N-[3-(4-fluorobenzoyl)-4,7-dihydro-5H-thieno[2,3-c]thi-opyran-2-yl]-2-(3-hydroxypiperidin-1-yl)acetamide;

N-{3-[(4-fluorophenyl)(hydroxy)methyl]-4,7-dihydro-5H-thieno[2,3-c]thiopyran-2-yl}-2-(3-hydroxypiperidin-1-yl)acetamide;

N-[3-(3,4-difluorobenzoyl)-4,7-dihydro-5H-thieno[2,3-c]thiopyran-2-yl]-2-(3-hydroxypiperidin-1-yl)acetamide;

N-[3-(3-fluorobenzoyl)-4,7-dihydro-5H-thieno[2,3-c]thi-opyran-2-yl]-2-piperidin-1-ylacetamide;

N-[3-(3-fluorobenzoyl)-4,7-dihydro-5H-thieno[2,3-c]thi-opyran-2-yl]-2-(3-hydroxypiperidin-1-yl)acetamide, N-{3-[(3-fluorophenyl)(hydroxy)methyl]-4,7-dihydro-5H-thieno[2,3-c]thiopyran-2-yl}-2-(3-hydroxypiperidin-1-yl)acetamide;

N-[3-(3-chlorobenzoyl)-4,7-dihydro-5H-thieno[2,3-c]pyran-2-yl]-2-(3-hydroxypiperidin-1-yl)acetamide;

N-{3-[(3-fluorophenyl)(hydroxy)methyl]-4,7-dihydro-5H-thieno[2,3-c]thiopyran-2-yl}-2-piperidin-1-ylacetamide;

N-{3-[hydroxy(4-methylphenyl)methyl]-4,7-dihydro-5H-thieno[2,3-c]pyran-2-yl}-2-piperidin-1-ylacetamide;

N-[3-(3-fluorobenzoyl)-4,7-dihydro-5H-thieno[2,3-c]pyran-2-yl]-2-piperidin-1-ylacetamide;

N-{3-[2-(3-fluorophenoxy)benzoyl]-4,7-dihydro-5H-thieno[2,3-c]thiopyran-2-yl}-2-piperidin-1-ylacetamide;

N-[3-(3-fluorobenzoyl)-4,7-dihydro-5H-thieno[2,3-c]pyran-2-yl]-2-(3-hydroxypiperidin-1-yl)acetamide;

N-{3-[2-(3-fluorophenoxy)benzoyl]-4,7-dihydro-5H-thieno[2,3-c]thiopyran-2-yl}-2-(3-hydroxypiperidin-1-yl)acetamide;

N-{3-[(3-fluorophenyl)(hydroxy)methyl]-4,7-dihydro-5H-thieno[2,3-c]pyran-2-yl}-2-piperidin-1-ylacetamide;

2-piperidin-1-yl-N-{3-[3-(trifluoromethyl)benzoyl]-4,7-dihydro-5H-thieno[2,3-c]pyran-2-yl}acetamide;

2-(3-hydroxypiperidin-1-yl)-N-{3-[3-(trifluoromethyl)benzoyl]-4,7-dihydro-5H-thieno[2,3-c]pyran-2-yl}acetamide;

N-[3-(1,1'-biphenyl-4-ylcarbonyl)-4,7-dihydro-5H-thieno[2,3-c]thiopyran-2-yl]-2-piperidin-1-ylacetamide;

N-(3-{hydroxy[3-(trifluoromethyl)phenyl]methyl}-4,7-dihydro-5H-thieno[2,3-c]pyran-2-yl)-2-piperidin-1-ylacetamide; and N-[3-(1,1'-biphenyl-4-ylcarbonyl)-4,7-dihydro-5H-thieno[2,3-c]thiopyran-2-yl]-2-(3-hydroxypiperidin-1-yl)acetamide.

EXAMPLE 18

Biological Activity of Selected Compounds

Selected compounds were evaluated for their anti-parasitic activity in a binding assay as described in U.S. Pat. No. 5,859,188 (Geary, et al., 1999). Results of the evaluations are given in Table 2 wherein "% Inhibition" means percent displacement of a radiolabelled ligand at 25 micromolar as described.

TABLE 2

| Compound | % Inhibition |
| --- | --- |
| 1 | 93–99 |
| 2 | 85–95 |
| 3 | 96–97 |
| 4 | 72–84 |

TABLE 2-continued

| Compound | % Inhibition |
| --- | --- |
| 5 | 52–54 |
| 6 | 64–70 |
| 7 | 76–78 |
| 8 | 90–92 |
| 9 | 51–77 |
| 10 | 21–38 |
| 11 | 59–85 |
| 12 | 83–87 |
| 13 | 49–70 |
| 14 | 25–35 |
| 15 | 0–18 |
| 16 | 37–42 |
| 17 | 15–37 |
| 18 | 70–85 |
| 19 | 59–67 |
| 20 | 86–88 |
| 21 | 38–47 |
| 23 | 22–28 |
| 24 | 11–58 |
| 25 | 31–48 |
| 26 | 90–91 |
| 27 | 77–96 |
| 28 | 11–79 |
| 29 | 88–95 |
| 30 | 14–68 |
| 31 | 28–32 |
| 32 | 73–87 |
| 33 | 92–94 |
| 34 | 100 |
| 35 | 80–81 |
| 36 | 92–94 |
| 37 | 0–66 |
| 38 | 68–73 |
| 39 | 49–50 |
| 40 | 100 |
| 41 | 97–100 |
| 42 | 100 |
| 43 | 100 |
| 44 | 34–43 |
| 45 | 82–83 |
| 46 | 32–41 |
| 47 | 55–62 |
| 48 | 54–55 |
| 49 | 46–55 |
| 50 | 81–87 |
| 51 | 84–86 |
| 52 | 84–92 |
| 53 | 19–20 |
| 54 | 93–97 |
| 55 | 100 |
| 56 | 99–100 |

Having described the invention in detail and by reference to the embodiments thereof, it will be apparent that modifications and variations are possible without departing from the scope of the appended claims.

What is claimed is:

1. A compound of Formula I comprising:

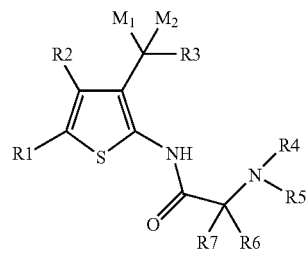

Formula I wherein:
- $R_1$ and $R_2$ are selected from the group consisting of H, alkyl, phenyl, substituted phenyl, benzyl, substituted benzyl, hetroaryl, substituted hetroaryl, hetroarylmethylene, and substituted hetroarylmethylene; or
- $R_1$ and $R_2$, along with the carbons to which they are attached, may form a 5- to 10-membered substituted or unsubstituted carbocyclic or heterocycloalkyl ring;
- $R_3$ is alkyl, heteroalkyl, cycloalkyl, substituted or unsubstituted aryl, or substituted or unsubstituted heteroaryl;
- $R_4$ and $R_5$ are independently H, alkyl, heteroalkyl, cycloalkyl, aryl, aralkyl, heteroaryl or heteroaralkyl;
- $R_4$ and $R_5$ taken together with the nitrogen to which they are attached, may form a 3- to 8-membered substituted or unsubstituted nitrogen containing ring;
- $R_6$ and $R_7$ are independently alkyl, heteroalkyl, aryl, aralkyl, heteroaryl or heteroaralkyl;
- $M_1$ is hydrogen and $M_2$ is —OH; or
- $M_1$ and $M_2$ taken together may form a carbonyl (C=O).

2. A compound according to claim 1 in which $R_1$ and $R_2$ form a 5- or 6-membered heterocycloalkyl ring containing a heteroatom selected from O, N, or S.

3. A compound according to claim 1 in which $R_1$ and $R_2$ are selected from H or alkyl.

4. A compound according to claim 1 in which $R_3$ is substituted or unsubstituted aryl.

5. A compound according to claim 1 in which $R_3$ is substituted or unsubstituted heteroaryl.

6. A compound according to claim 5 wherein the heteroaryl ring is 1-methyl-5-trifluromethy-1-pyrazolyl.

7. A compound according to claim 6 wherein the heteroaryl ring is 2-thienyl.

8. A compound according to claim 6 wherein the heteroaryl ring is 2-furyl.

9. A compound according to claim 1 in which $R_4$ and $R_5$ taken together form a 1-piperidinyl ring optionally substituted with —OH.

10. A compound according to claim 1 in which $R_7$ and $R_6$ are H.

11. A compound according to claim 1 selected from the group consisting of
- N-[3-(4-chlorobenzoyl)-4,7-dihydro-5H-thieno[2,3-c]pyran-2-yl]-2-piperidin-1-ylacetamide;
- N-{3-[(4-chlorophenyl)(hydroxy)methyl]-4,7-dihydro-5H-thieno[2,3-c]pyran-2-yl}-2-piperidin-1-ylacetamide;
- N-[3-(4-chlorobenzoyl)-4,7-dihydro-5H-thieno[2,3-c]pyran-2-yl]-2-(3-hydroxypiperidin-1-yl)acetamide;
- N-{3-[(4-chlorophenyl)(hydroxy)methyl]-4,7-dihydro-5H-thieno[2,3-c]pyran-2-yl}-2-(3-hydroxypiperidin-1-yl)acetamide;
- N-[5-ethyl-3-(4-methoxybenzoyl)thien-2-yl]-2-piperidin-1-ylacetamide;
- N-[5-ethyl-3-(4-methoxybenzoyl)thien-2-yl]-2-pyrrolidin-1-ylacetamide;
- N-[4-methyl-3-(benzoyl)thien-2-yl]-2-piperidin-1-ylacetamide;
- N-[4,5-dimethyl-3-(4-chlorobenzoyl)thien-2-yl]-2-piperidin-1-ylacetamide; N-[3-(4-chlorobenzoyl)-4,7-dihydro-5H-thieno[2,3-c]thiopyran-2-yl]-2-piperidin-1-ylacetamide;
- N-[3-(4-chlorobenzoyl)-4,7-dihydro-5H-thieno[2,3-c]thiopyran-2-yl]-2-(3-hydroxypiperidin-1-yl)acetamide;
- N-[3-(2-furoyl)-4,7-dihydro-5H-thieno[2,3-c]thiopyran-2-yl]-2-piperidin-1-ylacetamide;
- N-[3-(2-furoyl)-4,7-dihydro-5H-thieno[2,3-c]thiopyran-2-yl]-2-(3-hydroxypiperidin-1-yl)acetamide;
- methyl 4-({2-[(piperidin-1-ylacetyl)amino]-4,7-dihydro-5H-thieno[2,3-c]pyran-3-yl}carbonyl)benzoate;
- N-[3-(3-chlorobenzoyl)-4,7-dihydro-5H-thieno[2,3-c]pyran-2-yl]-2-piperidin-1-ylacetamide;
- N-[3-(2-furoyl)-4,7-dihydro-5H-thieno[2,3-c]pyran-2-yl]-2-piperidin-1-ylacetamide;
- N-[3-(2-furoyl)-4,7-dihydro-5H-thieno[2,3-c]pyran-2-yl]-2-(3-hydroxypiperidin-1-yl) acetamide;
- N-{3-[(4-chlorophenyl)sulfonyl]thien-2-yl}-2-piperidin-1-ylacetamide;
- N-[(2Z,3Z)-3-(4-chlorobenzylidene)-3,4,5,7-tetrahydro-2H-thieno[2,3-c]pyran-2-ylidene]-2-piperidin-1-ylacetamide;
- N-{3-[(4-chlorophenyl)(diethylamino)methyl]-4,7-dihydro-5H-thieno[2,3-c]pyran-2-yl}-2-piperidin-1-ylacetamide, dihydrochloride;
- N-{3-[(4-chlorophenyl)(hydroxy)methyl]-4,7-dihydro-5H-thieno[2,3-c]thiopyran-2-yl}-2-piperidin-1-ylacetamide;
- N-{3-[(4-chlorophenyl)(hydroxy)methyl]-4,7-dihydro-5H-thieno[2,3-c]thiopyran-2-yl}-2-(3-hydroxypiperidin-1-yl)acetamide;
- N-{3-[(4-chlorophenyl)(hydroxy)methyl]-4,7-dihydro-5H-thieno[2,3-c]thiopyran-2-yl}-2-(3-hydroxypiperidin-1-yl)acetamide;
- N-[3-(4-chlorobenzoyl)-4,7-dihydro-5H-thieno[2,3-c]pyran-2-yl]-2-[3-(hydroxymethyl)piperidin-1-yl]acetamide;
- N-[3-(4-chlorobenzoyl)-4,7-dihydro-5H-thieno[2,3-c]thiopyran-2-yl]-2-[3-(hydroxymethyl)piperidin-1-yl]acetamide;
- 2-azepan-1-yl-N-[3-(4-chlorobenzoyl)-4,7-dihydro-5H-thieno[2,3-c]thiopyran-2-yl]acetamide;
- 2-azepan-1-yl-N-{3-[(4-chlorophenyl)(hydroxy)methyl]-4,7-dihydro-5H-thieno[2,3-c]thiopyran-2-yl}acetamide;
- N-[3-(4-chlorobenzoyl)-4,7-dihydro-5H-thieno[2,3-c]thiopyran-2-yl]-N-methyl-2-piperidin-1-ylacetamide;
- 2-(3-hydroxypiperidin-1-yl)-N-[3-(4-methylbenzoyl)-4,7-dihydro-5H-thieno[2,3-c]pyran-2-yl]acetamide;
- N-[3-(4-methylbenzoyl)-4,7-dihydro-5H-thieno[2,3-c]pyran-2-yl]-2-piperidin-1-ylacetamide;
- N-[3-(4-methylbenzoyl)-4,7-dihydro-5H-thieno[2,3-c]thiopyran-2-yl]-2-piperidin-1-ylacetamide;
- 2-(3-hydroxypiperidin-1-yl)-N-[3-(4-methylbenzoyl)-4,7-dihydro-5H-thieno[2,3-c]thiopyran-2-yl]acetamide;
- N-[3-(3-chlorobenzoyl)-4,7-dihydro-5H-thieno[2,3-c]thiopyran-2-yl]-2-piperidin-1-ylacetamide;
- N-{3-[(3-chlorophenyl)(hydroxy)methyl]-4,7-dihydro-5H-thieno[2,3-c]thiopyran-2-yl}-2-(3-hydroxypiperidin-1-yl)acetamide;
- N-{3-[(3-chlorophenyl)(hydroxy)methyl]-4,7-dihydro-5H-thieno[2,3-c]thiopyran-2-yl}-2-(3-hydroxypiperidin-1-yl)acetamide;
- N-[3-(3-chlorobenzoyl)-4,7-dihydro-5H-thieno[2,3-c]thiopyran-2-yl]-2-(3-hydroxypiperidin-1-yl)acetamide;
- 2-(3-hydroxypiperidin-1-yl)-N-{3-[3-(trifluoromethyl)benzoyl]-4,7-dihydro-5H-thieno[2,3-c]thiopyran-2-yl}acetamide;
- 2-piperidin-1-yl-N-{3-[3-(trifluoromethyl)benzoyl]-4,7-dihydro-5H-thieno[2,3-c]thiopyran-2-yl}acetamide;
- 2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
- N-[3-(3,4-dichlorobenzoyl)-4,7-dihydro-5H-thieno[2,3-c]thiopyran-2-yl]-2-piperidin-1-ylacetamide;

N-[3-(2,2-dimethylpropanoyl)-4,7-dihydro-5H-thieno[2,3-c]thiopyran-2-yl]-2-(3-hydroxypiperidin-1-yl)acetamide;
2-piperidin-1-yl-N-[3-(thien-2-ylcarbonyl)-4,7-dihydro-5H-thieno[2,3-c]thiopyran-2-yl]acetamide;
2-(3-hydroxypiperidin-1-yl)-N-[3-(thien-2-ylcarbonyl)-4,7-dihydro-5H-thieno[2,3-c]thiopyran-2-yl]acetamide;
N-[3-(3,4-dichlorobenzoyl)-4,7-dihydro-5H-thieno[2,3-c]thiopyran-2-yl]-2-(3-hydroxypiperidin-1-yl)acetamide;
N-{3-[hydroxy(4-methylphenyl)methyl]-4,7-dihydro-5H-thieno[2,3-c]thiopyran-2-yl}-2-(3-hydroxypiperidin-1-yl)acetamide;
N-{3-[hydroxy(4-methylphenyl)methyl]-4,7-dihydro-5H-thieno[2,3-c]pyran-2-yl}-2-(3-hydroxypiperidin-1-yl)acetamide;
2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
2-(3-hydroxypiperidin-1-yl)-N-(3-{[1-methyl-5-(trifluoromethyl)-1H-pyrazol-4-yl]carbonyl}-4,7-dihydro-5H-thieno[2,3-c]thiopyran-2-yl)acetamide;
2-piperidin-1-yl-N-[3-(thien-2-ylcarbonyl)-4,7-dihydro-5H-thieno[2,3-c]pyran-2-yl]acetamide;
2-(3-hydroxypiperidin-1-yl)-N-[3-(thien-2-ylcarbonyl)-4,7-dihydro-5H-thieno[2,3-c]pyran-2-yl]acetamide;
N-(3-{[1-methyl-5-(trifluoromethyl)-1H-pyrazol-4-yl]carbonyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-(3-hydroxypiperidin-1-yl)acetamide;
2-(3-hydroxypiperidin-1-yl)-N-{3-[hydroxy(thien-2-yl)methyl]-4,7-dihydro-5H-thieno[2,3-c]thiopyran-2-yl}acetamide;
N-{3-[hydroxy(thien-2-yl)methyl]-4,7-dihydro-5H-thieno[2,3-c]thiopyran-2-yl}-2-piperidin-1-ylacetamide;
N-[3-(4-fluorobenzoyl)-4,7-dihydro-5H-thieno[2,3-c]thiopyran-2-yl]-2-piperidin-1-ylacetamide;
2-piperidin-1-yl-N-[3-(4-piperidin-1-ylbenzoyl)-4,7-dihydro-5H-thieno[2,3-c]thiopyran-2-yl]acetamide;
N-[3-(4-fluorobenzoyl)-4,7-dihydro-5H-thieno[2,3-c]thiopyran-2-yl]-2-(3-hydroxypiperidin-1-yl)acetamide;
N-{3-[(4-fluorophenyl)(hydroxy)methyl]-4,7-dihydro-5H-thieno[2,3-c]thiopyran-2-yl}-2-(3-hydroxypiperidin-1-yl)acetamide;
N-[3-(3,4-difluorobenzoyl)-4,7-dihydro-5H-thieno[2,3-c]thiopyran-2-yl]-2-(3-hydroxypiperidin-1-yl) acetamide;
N-[3-(3-fluorobenzoyl)-4,7-dihydro-5H-tbieno[2,3-c]thiopyran-2-yl]-2-piperidin-1-ylacetamide;
N-[3-(3-fluorobenzoyl)-4,7-dihydro-5H-thieno[2,3-c]thiopyran-2-yl]-2-(3-hydroxypiperidin-1-yl)acetamide;
N-{3-[(3-fluorophenyl)(hydroxy)methyl]-4,7-dihydro-5H-thieno[2,3-c]thiopyran-2-yl}-2-(3-hydroxypiperidin-1-yl) acetamide;
N-[3-(3-chlorobenzoyl)-4,7-dihydro-H-thieno[2,3-c]pyran-2-yl]-2-(3-hydroxypiperidin-1-yl)acetamide;
N-{3-[(3-fluorophenyl)(hydroxy)methyl]-4,7-dihydro-5H-thieno[2,3-c]thiopyran-2-yl}-2-piperidin-1-ylacetamide;
N-{3-[hydroxy(4-methylphenyl)methyl]-4,7-dihydro-5H-thieno[2,3-c]pyran-2-yl}-2-piperidin-1-ylacetamide;
N-[3-(3-fluorobenzoyl)-4,7-dihydro-5H-thieno[2,3-c]pyran-2-yl]-2-piperidin-1-ylacetamide;
N-{3-[2-(3-fluorophenoxy)benzoyl]-4,7-dihydro-5H-thieno[2,3-c]pyran-2-yl}-2-piperidin-1-ylacetamide;
N-[3-(3-fluorobenzoyl)-4,7-dihydro-H-thieno[2,3-c]pyran-2-yl]-2-(3-hydroxypiperidin-1-yl)acetamide;
N-{3-[2-(3-fluorophenoxy)benzoyl]-4,7-dihydro-5H-thieno[2,3-c]pyran-2-yl}-2-(3-hydroxypiperidin-1-yl)acetamide;
N-{3-[(3-fluorophenyl)(hydroxy)methyl]-4,7-dihydro-5H-thieno[2,3-c]pyran-2-yl}-2-piperidin-1-ylacetamide;
2-piperidin-1-yl-N-{3-[3-(trifluoromethyl)benzoyl]-4,7-dihydro-5H-thieno[2,3-c]pyran-2-yl}acetamide;
2-(3-hydroxypiperidin-1-yl)-N-{3-[3-(trifluoromethyl)benzoyl]-4,7-dihydro-5H-thieno[2,3-c]pyran-2-yl}acetamide;
N-[3-(1,1'-biphenyl-4-ylcarbonyl)-4,7-dihydro-5H-thieno[2,3-c]thiopyran-2-yl]-2-piperidin-1-ylacetamide;
N-(3-{hydroxy[3-(trifluoromethyl)phenyl]methyl}-4,7-dihydro-5H-thieno[2,3-c]pyran-2-yl)-2-piperidin-1-ylacetamide; and
N-[3-(, 1'-biphenyl-4-ylcarbonyl)-4,7-dihydro-5H-thieno[2,3-c]thiopyran-2-yl]-2-(3-hydroxypiperidin-1-yl)acetamide.

12. A composition comprising 1 to 3 compounds according to claim 1.

13. A composition comprising 1 to 3 compounds selected from the group consisting of:
N-[3-(4-chlorobenzoyl)-4,7-dihydro-5H-thieno[2,3-c]pyran-2-yl]-2-piperidin-1-ylacetamide;
N-{3-[(4-chlorophenyl)(hydroxy)methyl]-4,7-dihydro-5H-thieno[2,3-c]pyran-2-yl}-2-piperidin-1-ylacetamide;
N-[3-(4-chlorobenzoyl)-4,7-dihydro-5H-thieno[2,3-c]pyran-2-yl]-2-(3-hydroxypiperidin-1-yl)acetamide;
N-{3-[(4-chlorophenyl)(hydroxy)methyl]-4,7-dihydro-5H-thieno[2,3-c]pyran-2-yl}-2-(3-hydroxypiperidin-1-yl)acetamide;
N-[5-ethyl-3-(4-methoxybenzoyl)thien-2-yl]-2-piperidin-1-ylacetamide;
N-[5-ethyl-3-(4-methoxybenzoyl)thien-2-yl]-2-pyrrolidin-1-ylacetamide;
N-[4-methyl-3-(benzoyl)thien-2-yl]-2-piperidin-1-ylacetamide;
N-[4,5-dimethyl-3-(4-chlorobenzoyl)thien-2-yl]-2-piperidin-1-ylacetamide;
N-[3-(4-chlorobenzoyl)-4,7-dihydro-5H-thieno[2,3-c]thiopyran-2-yl]-2-piperidin-1-ylacetamide;
N-[3-(4-chlorobenzoyl)-4,7-dihydro-5H-thieno[2,3-c]thiopyran-2-yl]-2-(3-hydroxypiperidin-1-yl) acetamide;
N-[3-(2-furoyl)-4,7-dihydro-5H-thieno[2,3-c]thiopyran-2-yl]-2-piperidin-1-ylacetamide;
N-[3-(2-furoyl)-4,7-dihydro-5H-thieno[2,3-c]thiopyran-2-yl]-2-(3-hydroxypiperidin-1-yl)acetamide;
methyl 4-({2-[(piperidin-1-ylacetyl)amino]-4,7-dihydro-5H-thieno[2,3-c]pyran-3-yl} carbonyl)benzoate;
N-[3-(3-chlorobenzoyl)-4,7-dihydro-H-thieno[2,3-c]pyran-2-yl]-2-piperidin-1-ylacetamide;
N-[3-(2-furoyl)-4,7-dihydro-5H-thieno[2,3-c]pyran-2-yl]-2-piperidin-1-ylacetamide;

N-[3-(2-furoyl)-4,7-dihydro-5H-thieno[2,3-c]pyran-2-yl]-2-(3-hydroxypiperidin-1-yl)acetamide;
N-{3-[(4-chlorophenyl)sulfonyl]thien-2-yl}-2-piperidin-1-ylacetamide;
N-[(2Z,3Z)-3-(4-chlorobenzylidene)-3,4,5,7-tetrahydro-2H-thieno[2,3-c]pyran-2-ylidene]-2-piperidin-1-ylacetamide;
N-{3-[(4-chlorophenyl)(diethylamino)methyl]-4,7-dihydro-5H-thieno[2,3-c]pyran-2-yl}-2-piperidin-1-ylacetamide, dihydrochloride;
N-{3-[(4-chlorophenyl)(hydroxy)methyl]-5H-thieno[2,3-c]thiopyran-2-yl}-2-piperidin-1-ylacetamide;
N-{3-[(4-chlorophenyl)(hydroxy)methyl]-4,7-dihydro-5H-thieno[2,3-c]thiopyran-2-yl}-2-(3-hydroxypiperidin-1-yl)acetamide;
N-{3-[(4-chlorophenyl)(hydroxy)methyl]-4,7-dihydro-5H-thieno[2,3-c]thiopyran-2-yl}-2-(3-hydroxypiperidin-1-yl)acetamide;
N-[3-(4-chlorobenzoyl)-4,7-dihydro-5H-thieno[2,3-c]pyran-2-yl]-2-[3-(hydroxymethyl)piperidin-1-yl]acetamide;
N-[3-(4-chlorobenzoyl)-4,7-dihydro-5H-thieno[2,3-c]thiopyran-2-yl]-2-[3-(hydroxymethyl)piperidin-1-yl]acetamide;
2-azepan-1-yl-N-[3-(4-chlorobenzoyl)-4,7-dihydro-H-thieno[2,3-c]thiopyran-2-yl]acetamide;
2-azepan-1-yl-N-{3-[(4-chlorophenyl)(hydroxy)methyl]-4,7-dihydro-5H-thieno[2,3-c]thiopyran-2-yl}acetamide;
N-[3-(4-chlorobenzoyl)-4,7-dihydro-5H-thieno[2,3-c]thiopyran-2-yl]-N-methyl-2-piperidin-1-ylacetamide;
2-(3-hydroxypiperidin-1-yl)-N-[3-(4-methylbenzoyl)-4,7-dihydro-5H-thieno[2,3-c]pyran-2-yl]acetamide;
N-[3-(4-methylbenzoyl)-4,7-dihydro-5H-thieno[2,3-c]pyran-2-yl]-2-piperidin-1-ylacetamide;
N-[3-(4-methylbenzoyl)-4,7-dihydro-5H-thieno[2,3-c]thiopyran-2-yl]-2-piperidin-1-ylacetamide;
2-(3-hydroxypiperidin-1-yl)-N-[3-(4-methylbenzoyl)-4,7-dihydro-5H-thieno[2,3-c]thiopyran-2-yl]acetamide;
N-[3-(3-chlorobenzoyl)-4,7-dihydro-5H-thieno[2,3-c]thiopyran-2-yl]-2-piperidin-1-ylacetamide;
N-{3-[(3-chlorophenyl)(hydroxy)methyl]-4,7-dihydro-5H-thieno[2,3-c]thiopyran-2-yl}-2-(3-hydroxypiperidin-1-yl)acetamide;
N-{3-[(3-chlorophenyl)(hydroxy)methyl]-4,7-dihydro-5H-thieno[2,3-c]thiopyran-2-yl}-2-(3-hydroxypiperidin-1-yl)acetamide;
N-[3-(3-chlorobenzoyl)-4,7-dihydro-5H-thieno[2,3-c]thiopyran-2-yl]-2-(3-hydroxypiperidin-1-yl)acetamide;
2-(3-hydroxypiperidin-1-yl)-N-{3-[3-(trifluoromethyl)benzoyl]-4,7-dihydro-5H-thieno[2,3-c]thiopyran-2-yl}acetamide;
2-piperidin-1-yl-N-{3-[3-(trifluoromethyl)benzoyl]-4,7-dihydro-5H-thieno[2,3-c]thiopyran-2-yl}acetamide;
2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
N-[3-(3,4-dichlorobenzoyl)-4,7-dihydro-5H-thieno[2,3-c]thiopyran-2-yl]-2-piperidin-1-ylacetamide;
N-[3-(2,2-dimethylpropanoyl)-4,7-dihydro-5H-thieno[2,3-c]thiopyran-2-yl]-2-(3-hydroxypiperidin-1-yl)acetamide;
2-piperidin-1-yl-N-[3-(thien-2-ylcarbonyl)-4,7-dihydro-5H-thieno[2,3-c]thiopyran-2-yl]acetamide;
2-(3-hydroxypiperidin-1-yl)-N-[3-(thien-2-ylcarbonyl)-4,7-dihydro-5H-thieno[2,3-c]thiopyran-2-yl]acetamide;

N-[3-(3,4-dichlorobenzoyl)-4,7-dihydro-5H-thieno[2,3-c]thiopyran-2-yl]-2-(3-hydroxypiperidin-1-yl)acetamide;
N-{3-[hydroxy(4-methylphenyl)methyl]-4,7-dihydro-5H-thieno[2,3-c]thiopyran-2-yl}-2-(3-hydroxypiperidin-1-yl)acetamide;
N-{3-[hydroxy(4-methylphenyl)methyl]-4,7-dihydro-5H-thieno[2,3-c]pyran-2-yl}-2-(3-hydroxypiperidin-1-yl)acetamide;
2-(3-hydroxypiperidin-1-yl)-N-(3-{hydroxy[3-(trifluoromethyl)phenyl]methyl}-4,7-dihydro-5H-thieno[2,3-c]thiopyran-2-yl)acetamide;
2-(3-hydroxypiperidin-1-yl)-N-(3-{[1-methyl-5-(trifluoromethyl)-1H-pyrazol-4-yl]carbonyl}-4,7-dihydro-5H-thieno[2,3-c]thiopyran-2-yl)acetamide;
2-piperidin-1-yl-N-[3-(thien-2-ylcarbonyl)-4,7-dihydro-5H-thieno[2,3-c]pyran-2-yl]acetamide;
2-(3-hydroxypiperidin-1-yl)-N-[3-(thien-2-ylcarbonyl)-4,7-dihydro-5H-thieno[2,3-c]pyran-2-yl]acetamide;
N-(3-{[1-methyl-5-(trifluoromethyl)-1H-pyrazol-4-yl]carbonyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-piperidin-1-ylacetamide;
N-(3-{hydroxy[1-methyl-5-(trifluoromethyl)-1H-pyrazol-4-yl]methyl}-4,7-dihydro-5H-thieno[2,3-c]thiopyran-2-yl)-2-(3-hydroxypiperidin-1-yl)acetamide;
2-(3-hydroxypiperidin-1-yl)-N-{3-[hydroxy(thien-2-yl)methyl]-4,7-dihydro-5H-thieno[2,3-c]thiopyran-2-yl}acetamide;
N-{3-[hydroxy(thien-2-yl)methyl]-4,7-dihydro-5H-thieno[2,3-c]thiopyran-2-yl}-2-piperidin-1-ylacetamide;
N-[3-(4-fluorobenzoyl)-4,7-dihydro-5H-thieno[2,3-c]thiopyran-2-yl]-2-piperidin-1-ylacetamide;
2-piperidin-1-yl-N-[3-(4-piperidin-1-ylbenzoyl)-4,7-dihydro-5H-thieno[2,3-c]thiopyran-2-yl]acetamide;
N-[3-(4-fluorobenzoyl)-4,7-dihydro-5H-thieno[2,3-c]thiopyran-2-yl]-2-(3-hydroxypiperidin-1-yl)acetamide;
N-{3-[(4-fluorophenyl)(hydroxy)methyl]-4,7-dihydro-5H-thieno[2,3-c]thiopyran-2-yl}-2-(3-hydroxypiperidin-1-yl)acetamide;
N-[3-(3,4-difluorobenzoyl)-4,7-dihydro-5H-thieno[2,3-c]thiopyran-2-yl]-2-(3-hydroxypiperidin-1-yl)acetamide;
N-[3-(3-fluorobenzoyl)-4,7-dihydro-5H-thieno[2,3-c]thiopyran-2-yl]-2-piperidin-1-ylacetamide,
N-[3-(3-fluorobenzoyl)-4,7-dihydro-5H-thieno[2,3-c]thiopyran-2-yl]-2-(3-hydroxypiperidin-1-yl)acetamide;
N-{3-[(3-fluorophenyl)(hydroxy)methyl]-4,7-dihydro-5H-thieno[2,3-c]thiopyran-2-yl}-2-(3-hydroxypiperidin-1-yl)acetamide;
N-[3-(3-chlorobenzoyl)-4,7-dihydro-5H-thieno[2,3-c]pyran-2-yl]-2-(3-hydroxypiperidin-1-yl)acetamide;
N-{3-[(3-fluorophenyl)(hydroxy)methyl]-4,7-dihydro-5H-thieno[2,3-c]thiopyran-2-yl}-2-piperidin-1-ylacetamide;
N-{3-[hydroxy(4-methylphenyl)methyl]-4,7-dihydro-5H-thieno[2,3-c]pyran-2-yl}-2-piperidin-1-ylacetamide;
N-[3-(3-fluorobenzoyl)-4,7-dihydro-5H-thieno[2,3-c]pyran-2-yl]-2-piperidin-1-ylacetamide;
N-{3-[2-(3-fluorophenoxy)benzoyl]-4,7-dihydro-5H-thieno[2,3-c]thiopyran-2-yl}-2-piperidin-1-ylacetamide;
N-[3-(3-fluorobenzoyl)-4,7-dihydro-5H-thieno[2,3-c]pyran-2-yl]-2-(3-hydroxypiperidin-1-yl)acetamide;

N-{3-[2-(3-fluorophenoxy)benzoyl]-4,7-dihydro-5H-thieno[2,3-c]thiopyran-2-yl}-2-(3-hydroxypiperidin-1-yl)acetamide;

N-{3-[(3-fluorophenyl)(hydroxy)methyl]-4,7-dihydro-5H-thieno[2,3-c]pyran-2-yl}-2-piperidin-1-ylacetamide;

2-piperidin-1-yl-N-{3-[3-(trifluoromethyl)benzoyl]-4,7-dihydro-5H-thieno[2,3-c]pyran-2-yl}acetamide;

2-(3-hydroxypiperidin-1-yl)-N-{3-[3-(trifluoromethyl)benzoyl]-4,7-dihydro-5H-thieno[2,3-c]pyran-2-yl}acetamide;

N-[3-(1,1'-biphenyl-4-ylcarbonyl)-4,7-dihydro-5H-thieno[2,3-c]thiopyran-2-yl]-2-piperidin-1-ylacetamide;

N-(3-{hydroxy[3-(trifluoromethyl)phenyl]methyl}-4,7-dihydro-5H-thieno[2,3-c]pyran-2-yl)-2-piperidin-1-ylacetamide; and N-[3-(1,1'-biphenyl-4-ylcarbonyl)-4,7-dihydro-5H-thieno[2,3-c]pyran-2-yl]-2-(3-hydroxypiperidin-1-yl)acetamide.

14. A method of treating or preventing parasitic diseases in mammals comprising administering to a mammal in need thereof a composition comprising 1 to three compounds according to claim 1.

* * * * *